US007951784B2

(12) United States Patent
Rana et al.

(10) Patent No.: US 7,951,784 B2
(45) Date of Patent: May 31, 2011

(54) RNA INTERFERENCE AGENTS FOR THERAPEUTIC USE

(75) Inventors: Tariq M. Rana, San Diego, CA (US); Zuoshang Xu, Wellesley, MA (US)

(73) Assignee: University of Massachusetts, Boston, MA (US)

( * ) Notice: Subject to any disclaimer, the term of this patent is extended or adjusted under 35 U.S.C. 154(b) by 495 days.

(21) Appl. No.: 11/698,785

(22) Filed: Jan. 26, 2007

(65) Prior Publication Data

US 2008/0125386 A1    May 29, 2008

Related U.S. Application Data

(60) Provisional application No. 60/762,957, filed on Jan. 26, 2006, provisional application No. 60/762,956, filed on Jan. 26, 2006, provisional application No. 60/762,951, filed on Jan. 26, 2006.

(51) Int. Cl.
*A61K 31/70* (2006.01)
*C07H 21/04* (2006.01)

(52) U.S. Cl. ......................................... 514/44; 536/24.5
(58) Field of Classification Search ........................ None
See application file for complete search history.

(56) References Cited

U.S. PATENT DOCUMENTS

| | | | |
|---|---|---|---|
| 6,592,845 B2 | 7/2003 | Uckun et al. | |
| 2003/0143732 A1* | 7/2003 | Fosnaugh et al. | 435/325 |
| 2005/0020521 A1 | 1/2005 | Rana | |
| 2005/0181382 A1* | 8/2005 | Zamore et al. | 435/6 |
| 2006/0008822 A1 | 1/2006 | Manoharan et al. | |
| 2006/0009409 A1 | 1/2006 | Woolf | |
| 2006/0069050 A1 | 3/2006 | Rana | |
| 2006/0229268 A1* | 10/2006 | Benjamin et al. | 514/44 |

FOREIGN PATENT DOCUMENTS

| | | |
|---|---|---|
| WO | 2004/080406 A2 | 9/2004 |
| WO | 2005/028650 A2 | 3/2005 |
| WO | 2005/079533 A2 | 9/2005 |

OTHER PUBLICATIONS

Asoh, Sadamitsu et al., "Protection against ischemic brain injury by protein therapeutics," *PNAS*, vol. 99(26):17107-17112 (2002).
Baulcombe, David, "RNA silencing in plants," *Nature*, vol. 431:356-363 (2004).
Beal, M. Flint, "Energetics in the pathogenesis of neurodegenerative diseases," *Trends Neurosci.*, vol. 23:298-304 (2000).
Beal, M. Flint, "Mitochondria and oxidative damage in amyotrophic lateral sclerosis," *Functional Neurology*, vol. 16(Suppl.):161-169 (2001).
Beckman, Jospeh S. et al., "ALS, SOD and peroxynitrite," *Nature*, vol. 364:584 (1993).
Behndig, Anders et al., "In vitro photochemical cataract in mice lacking copper-zinc superoxide dismutase," *Free Radical Biology & Medicine*, vol. 31(6):738-744 (2001).

Bittigau, Petra et al., "Glutamate in Neurologic Diseases," *J. Child Neurol.*, vol. 12:471-485 (1997).
Borchelt, David R. et al., "Superoxide Dismutase 1 Subunits with Mutations Linked to Familial Amyotrophic Lateral Sclerosis Do Not Affect Wild-type Subunit Function," *The Journal of Biological Chemistry*, vol. 270(7):3234-3238 (1995).
Borchelt, David R. et al., "Superoxide dismutase 1 with mutations linked to familial amyotrophic lateral sclerosis possesses significant activity," *Proc. Natl. Acad. Sci. USA*, vol. 91:8292-8296 (1994).
Bridge, Alan J. et al., "Induction of an interferon response by RNAi vectors in mammalian cells," *Nature Genetics Advance Online Publication*, pp. 1-2 (2003).
Brown, Kirk M. et al., "Target accessibility dictates the potency of human RISC," *Nature Structural & Molecular Biology*, vol. 12(5):469-470 (2005).
Bruijn, Lucie I. et al., "Aggregation and Motor Neuron Toxicity of an ALS-Linked SOD1 Mutant Independent from Wild-Type SOD1," *Science*, vol. 281:1851-1854 (1998).
Bruijn, L.I. et al., "Elevated free nitrotyrosine levels, but not protein-bound nitrotyrosine or hydroxyl radicals, throughout amyotrophic lateral sclerosis (ALS)-like disease implicate tyrosine nitration as an aberrant in vivo property of one familial ALS-linked superoxide dismutase 1 mutant," *Proc. Natl. Acad. Sci. USA*, vol. 94:7606-7611 (1997).
Brummelkamp, Thijn R. et al., "Stable suppression of tumorigenicity by virus-mediated RNA interference," *Cancer Cell*, vol. 2:243-247 (2002).
Cai, Huaibin et al., "BACE1 is the major β-secretase for generation of Aβ peptides by neurons," *Nature Neuroscience*, vol. 4(3):233-234 (2001).
Cao, Guodong et al., "In Vivo Delivery of a Bcl-xL Fusion Protein Containing the TAT Protein Transduction Domain Protects against Ischemic Brain Injury and Neuronal Apoptosis," *The Journal of Neuroscience*, vol. 22(13):5423-5431 (2002).
Caplen, Natasha J. et al., "Specific inhibition of gene expression by small double-stranded RNAs in invertebrate and vertebrate systems," *PNAS*, vol. 98(17):9742-9747 (2001).
Carrington, James C., "Small RNAs and Arabidopsis. A Fast Forward Look," *Plant Physiology*, vol. 138:565-566 (2005).
Chiu, Ya-Lin et al., "Inhibition of Human Immunodeficiency Virus Type 1 Replication by RNA Interference Directed against Human Transcription Elongation Factor P-TEFb (CDK9/CyclinT1)," *Journal of Virology*, vol. 78(5):2517-2529 (2004).
Chiu, Ya-Lin et al., "RNAi in Human Cells: Basic Structural and Functional Features of Small Interfering RNA," *Molecular Cell*, vol. 10:549-561 (2002).
Chiu, Ya-Lin et al., "siRNA function in RNAi: A chemical modificaion analysis," *RNA*, vol. 9:1034-1048 (2003).

(Continued)

*Primary Examiner* — Tracy Vivlemore
(74) *Attorney, Agent, or Firm* — Nelson Mullins Riley & Scarborough LLP; Debra J. Milasincic, Esq.; Pankaj N. Desai

(57) ABSTRACT

The invention features chemically modified small interfering RNAs (siRNAs) that are stable in vivo and retain the ability to form an A-form helix when in association with a target RNA. The features siRNA are effective therapeutics, particularly for targeting SOD1.

1 Claim, 8 Drawing Sheets

OTHER PUBLICATIONS

Chiu, Ya-Lin et al., "Visualizing a Correlation between siRNA Localization, Cellular Uptake, and RNAi in Living Cells," *Chemistry & Biology*, vol. 11:1165-1175 (2004).
Cho, Sarah S. et al., "Activation of STAT4 by IL-12 and IFN-α," *The Journal of Immunology*, vol. 157:4781-4789 (1996).
Crow, John P. et al., "Decreased Zinc Affinity of Amyotrophic Lateral Sclerosis-Associated Superoxide Dismutase Mutants Leads to Enhanced Catalysis of Tyrosine Nitration by Peroxynitrite," *Journal of Neurochemistry*, vol. 69:1936-1944 (1997).
Cummins, Lendell L. et al., "Characterization of fully 2'-modified oligoribonucleotide hetero- and homoduplex hybridization and nuclease sensitivity," *Nucleic Acids Research*, vol. 23(11):2019-2024 (1995).
Davidson, Beverly L. et al., "Molecular medicine for the brain: silencing of disease genes with RNA interference," *The Lancet Neurology*, vol. 3:145-149 (2004).
Denovan-Wright, EM et al., "RNAi: a potential therapy for the dominantly inherited nucleotide repeat diseases," *Gene Therapy*, vol. 13:525-531 (2006).
Dietz, Gunnar P. H. et al., "Inhibition of Neuronal Apoptosis in Vitro and in Vivo Usint TAT-Mediated Protein Transduction," *Molecular and Cellular Neuroscience*, vol. 21:29-37 (2002).
Ding, Hongliu et al., "Selective silencing by RNAi of a dominant allele that causes amyotrophic lateral sclerosis," *Aging Cell*, vol. 2:209-217 (2003).
Dufès, Christine et al., "Dendrimers in gene delivery," *Advanced Drug Delivery Reviews*, vol. 57:2177-2202 (2005).
Dykxhoorn, Derek M. et al., "The Silent Revolution: RNA Interference as Basic Biology, Research Tool, and Therapeutic," *Annu. Rev. Med.*, vol. 56:401-423 (2005).
Dykxhoorn, DM et al., "The silent treatment: siRNAs as small molecule drugs," *Gene Therapy*, vol. 13:541-552 (2006).
Elbashir, Sayda M. et al., "Duplexes of 21-nucleotide RNAs mediate RNA interference in cultured mammalian cells," *Nature*, vol. 411:494-498 (2001).
Elbashir, Sayda M. et al., "Functional anatomy of siRNAs for mediating efficient RNAi in *Drosophila melanogaster* embryo lysate," *The EMBO Journal*, vol. 20(23):6877-6888 (2001).
Elchuri, Sailaja et al., "CuZnSOD deficiency leads to persistent and widespread oxidative damage and hepatocarcinogenesis later in life," *Oncogene*, vol. 24:367-380 (2005).
Estévez, Alvaro G. et al., "Induction of Nitric Oxide-Dependent Apoptosis in Motor Neurons by Zinc-Deficient Superoxide Dismutase," *Science*, vol. 286:2498-2500 (1999).
Filipowicz, Witold, "RNAi: The Nuts and Bolts of the RISC Machine," *Cell*, vol. 122:17-20 (2005).
Fire, Andrew et al., "Potent and specific genetic interference by double-stranded RNA in *Caenorhabditis elegans*," *Nature*, vol. 391:806-811 (1998).
Flood, Dorothy G. et al., "Hindlimb Motor Neurons Require Cu/Zn Superoxide Dismutase for Maintenance of Neuromuscular Junctions," *American Journal of Pathology*, vol. 155(2):663-672 (1999).
Fridovich, I., "Superoxide dismutases," *Advances in Enzymology & Related Areas of Molecular Biology*, vol. 58:61-97 (1986).
Guégan, Christelle et al., "Recruitment of the Mitochondrial-Dependent Apoptotic Pathway in Amyotrophic Lateral Sclerosis," *The Journal of Neuroscience*, vol. 21(17):6569-6576 (2001).
Gurney, Mark E. et al., "Motor Neuron Degeneration in Mice That Express a Human Cu,Zn Superoxide Dismutase Mutation," *Science*, vol. 264:1772-1775 (1994).
Haass, Christian et al., "Alzheimer disease γ-secretase: a complex story of GxGD-type presenilin proteases," *Trends in Cell Biology*, vol. 12(12):556-562 (2002).
Haley, Benjamin et al., "Kinetic analysis of the RNAi enzyme complex," *Nat. Struct. Mol. Biol.*, vol. 11(7):599-606 (2004).
Hannon, Gregory J., "RNA interference," *Nature*, vol. 418:244-251 (2002).
Hannon, Gregory J. et al., "Unlocking the potential of the human genome with RNA interference," *Nature*, vol. 431:371-278 (2004).
Harper, Scott Q. et al., "RNA interference improves motor and neuropathological abnormalities in a Huntington's disease mouse model," *PNAS*, vol. 102(16):5820-5825 (2005).
Hass, Michael A. et al., "Rat Lung Cu,Zn Superoxide Dismutase," *J. Clin. Invest.*, vol. 83:1241-1246 (1989).
Hart, Stephen L., "Lipid Carriers for Gene Therapy," *Current Drug Delivery*, vol. 2:423-428 (2005).
He, Lin et al., "A microRNA polycistron as a potential human oncogene," *Nature*, vol. 435:828-833 (2005).
Ho, Ye-Shih et al., "cDNA and deduced amino acid sequence of rat copper-zinc-containing superoxide dismutase," *Nucleic Acids Research*, vol. 15(16):6746 (1987).
Hornung, Veit et al., "Sequence-specific potent induction of IFN-α by short interfering RNA in plasmacytoid dendritic cells through TLR7," *Nature Medicine*, vol. 11(3):263-270 (2005).
Hutvágner, György et al., "A microRNA in a Multiple-Turnover RNAi Enzyme Comples," *Science*, vol. 297:2056-2060 (2002).
Hutvágner, György et al., "Sequence-Specific Inhibition of Small RNA Function," *PLoS Biology*, vol. 2(4):465-475 (2004).
Hwang, Seongwoo et al., "Discovery of a Small Molecule Tat-*trans*-Activation-responsive RNA Antagonist That Potently Inhibits Human Immunodeficiency Virus-1 Replication," *The Journal of Biological Chemistry*, vol. 278(40):39092-39103 (2003).
Ikonomidou, Chrysanthy et al., "Motor Neuron Degeneration Induced by Excitotoxin Agonists Has Features in Common with those Seen in the SOD-1 Transgenic Mouse Model of Amyotrophic Lateral Sclerosis," *Journal of Neuropathology and Experimental Neurology*, vol. 55(2):211-224 (1996).
Ikonomidou, Chrysanthy et al., "Neurodegenerative Disorders: Clues from Glutamate and Energy Metabolism," *Critical Reviews in Neurobiology*, vol. 10(2):239-263 (1996).
Jackson, Aimee L. et al., "Expression profiling reveals off-target gene regulation by RNAi," *Nature Biotechnology*, vol. 21(6):635-637 (2003).
Jackson, Aimee L. et al., "Noise amidst the silence: off-target effects of siRNAs?" *Trends in Genetics*, vol. 20(11):521-524 (2004).
Johnson, Steven M. et al., "*RAS* is Regulated by the *let-7* MicroRNA Family," *Cell*, vol. 120:635-647 (2005).
Johnston, Jennifer A. et al., "Formation of high molecular weight complexes of mutant Cu,Zn-superoxide dismutase in a mouse model for familial amyotrophic lateral sclerosis," *PNAS*, vol. 97(23):12571-12576 (2000).
Judge, Adam D. et al., "Sequence-dependent stimulation of the mammalian innate immune response by synthetic siRNA," *Nature Biotechnology*, vol. 23(4):457-462 (2005).
Kawase, Makoto et al., "Exacerbation of Delayed Cell Injury After Transient Global Ischemia in Mutant Mice with CuZn Superoxide Dismutase Deficiency," *Stroke*, vol. 30:1962-1968 (1999).
Khvorova, Anastasia et al., "Functional siRNAs and miRNAs Exhibit Strand Bias," *Cell*, vol. 115:209-216 (2003).
Kilic, Ertugrul et al., "Intravenous TAT-Bcl-XL is Protective after Middle Cerebral Artery Occlusion in Mice," *Ann. Neurol.*, vol. 52:617-622 (2002).
Kloosterman, Wigard P. et al., "In situ detection of miRNAs in animal ambryos using LNA-modified oligonucleotide probes," *Nature Methods*, vol. 3(1):27-29 (2006).
Kondo, Takeo et al., "Reduction of CuZn-Superoxide Dismutase Activity Exacerbates Neuronal Cell Injury and Edema Formation after Transient Focal Cerebral Ischemia," *The Journal of Neuroscience*, vol. 17(11):4180-4189 (1997).
Lee, Sheu-Fen et al., "Mammalian APH-1 Interacts with Presenilin and Nicastrin and Is Required for Intramembrane Proteosysis of Amyloid-β Precursor Protein and Notch," *The Journal of Biological Chemistry*, vol. 277(47):45013-45019 (2002).
Liaw, W.-J. et al., "Knockdown of Spinal Cord Postsynaptic Density Protein-95 Prevents the Development of Morphine Tolerance in Rats," *Neuroscience*, vol. 123:11-15 (2004).
Lieberman, Judy et al., "Interfering with disease: opportunities and roadblocks to harnessing RNA interference," *Trends in Molecular Medicine*, vol. 9(9):397-403 (2003).
Liu, Jidong et al., "Argonaute2 is the Catalytic Engine of Mammalian RNAi," *Science*, vol. 305:1437-1441 (2004).
Lu, Jun et al., "MicroRNA expression profiles classify human cancers," *Nature*, vol. 435:834-838 (2005).

Luo, Yi et al., "Mice deficient in BACE1, the Alzheimer's β-secretase, have normal phenotype and abolished β-amyloid generation," *Nature Neuroscience*, vol. 4(3):231-232 (2001).

Ma, Jin-Biao et al., "Structural basis for 5'-end-specific recognition of guide RNA by the *A. fulgidus* Piwi protein," *Nature*, vol. 434:666-670 (2005).

Matz, Paul G. et al., "Cell Death After Exposure to Subarachnoid Hemolysate Correlates Inversely With Expression of CuZn-Superoxide Dismutase," *Stroke*, vol. 31:2450-2458 (2000).

Matzuk, Martin M. et al., "Ovarian Function in Superoxide Dismutase 1 and 2 Knockout Mice," *Endocrinology*, vol. 139(9):4008-4011 (1998).

McFadden, Sandra L. et al., "Anatomical, Metabolic and Genetic Aspects of Age-related Hearing Loss in Mice," *Audiology*, vol. 40:313-321 (2001).

Meister, Gunter et al., "Human Argonaute2 Mediates RNA Cleavage Targeted by miRNAs and siRNAs," *Molecular Cell*, vol. 15:185-197 (2004).

Meister, Gunter et al., "Mechanisms of gene silencing by double-stranded RNA," *Nature*, vol. 431:343-349 (2004).

Menzies, Fiona M. et al., "Mitochondrial dysfunction in a cell culture model of familial amyotrophic lateral sclerosis," *Brain*, vol. 125:1522-1533 (2002).

Morrissey, David V. et al., "Potent and persistent in vivo anti-HBV activity of chemically modified siRNAs," *Nature Biotechnology Advance Online Publication*, pp. 1-6 (2005).

Nelson, Peter T. et al., "RAKE and LNA-ISH reveal microRNA expression and localization in archival human brain," *RNA*, vol. 12:187-191 (2006).

Novina, Carl D. et al., "The RNAi revolution," *Nature*, vol. 430:161-164 (2004).

Ohki, E.C. et al., "Improving the transfection efficiency of post-mitotic neurons," *Journal of Neuroscience Methods*, vol. 112:95-99 (2001).

Palliser, Deborah et al., "An siRNA-based microbicide protects mice from lethal herpes simplex virus 2 infection," *Nature*, vol. 439:89-94 (2006).

Parker, James S. et al., "Structural insights into mRNA recognition from a PIWI domain-siRNA guide complex," *Nature*, vol. 434:663-666 (2005).

Pebernard, Stephanie et al., "Determinants of interferon-stimulated gene induction by RNAi vectors," *Differentiation*, vol. 72:103-111 (2004).

Ping, Yueh-Hsin et al., "Dynamics of RNA-protein interactions in the HIV-1 Rev-RRE complex visualized by 6-thioguanosine-mediated photocrosslinking," *RNA*, vol. 3:850-860 (1997).

Poy, Matthew N. et al., "A pancreatic islet-specific microRNA regulates insulin secretion," *Nature*, vol. 432:226-230 (2004).

Ralph, G. Scott et a., "Silencing mutant SOD1 using RNAi protects against neurodegeneration and extends survival in an ALS model," *Nature Medicine*, vol. 11:429-433 (2005).

Rana, Tariq M. et al., "Biochemical and Functional Interactions between HIV-1 Tat Protein and TAR RNA," *Archives of Biochemistry and Biophysics*, vol. 365(2):175-185 (1999).

Raoul, Cédric et al., "Lentiviral-mediated silencing of SOD1 through RNA interference retards disease onset and progression in a mouse model of ALS," *Nature Medicine*, vol. 11(4):423-428 (2005).

Reaume, Andrew G. et al., "Motor neurons in Cu/Zn superoxide dismutase-deficient mice develop normally but exhibit enhanced cell death after axonal injury," *Nature Genetics*, vol. 13:43-47 (1996).

Reynolds, Angela et al., "Rational siRNA design for RNA interference," *Nature Biotechnology*, vol. 22(3):326-330 (2004).

RGD Gene Report, "Sod1," retrieved online at http://rgd.mcw.edu/tools/genes/genes_view/cgi?id=3731.

Richter, Sara et al., "TAR RNA loop: A scaffold for the assembly of a regulatory switch in HIV replication," *PNAS*, vol. 99(12):7928-7933 (2002).

Ripps, Michael E. et al., "Transgenic mice expressing an altered murine superoxide dismutase gene provide an animal model of amyotrophic lateral sclerosis," *Proc. Natl. Acad. Sci. USA*, vol. 92:689-693 (1995).

Rivas, Fabiola V. et al., "Purified Argonaute2 and an siRNA form recombinant human RISC," *Nature Structural & Molecular Biology*, vol. 12(4):340-349 (2005).

Roberds, Steven L. et al., "BACE knockout mice are healthy despite lacking the primary β-secretase activity in brain: implications for Alzheimer's disease therapeutics," *Human Molecular Genetics*, vol. 10(12):1317-1324 (2001).

Rodriguez, Jorge A. et al., "Familial Amyotrophic Lateral Sclerosis-associated Mutations Decrease the Thermal Stability of Distinctly Metallated Species of Human Copper/Zinc Superoxide Dismutase," *The Journal of Biological Chemistry*, vol. 277 (18):15932-15937 (2002).

Rossi, John J., "A cholesterol connection in RNAi," *Nature*, vol. 432:155-156 (2004).

Rossi, JJ, "SNALPing siRNAs in vivo," *Gene Therapy*, vol. 13:583-584 (2006).

Rothstein, Jeffrey D., "Excitotoxicity hypothesis," *Neurology*, vol. 47(Suppl. 2):S19-S26 (1996).

Rubinson, Douglas A. et al., "A lentivirus-based system to functionally silence genes in primary mammalian cells, stem cells and transgenic mice by RNA interference," *Nature Genetics*, vol. 33:401-406 (2003).

Saito, Yuki et al., "Transgenic Small Interfering RNA Halts Amyotrophic Lateral Sclerosis in a Mouse Model," *The Journal of Biological Chemistry*, vol. 280(52):42826-42830 (2005).

Scacheri, Peter C. et al., "Short interfering RNAs can induce unexpected and divergent changes in the levels of untargeted proteins in mammalian cells," *PNAS*, vol. 101(7):1892-1897 (2004).

Schwarz, Dianne S. et al., "Asymmetry in the Assembly of the RNAi Enzyme Complex," *Cell*, vol. 115:199-208 (2003).

Scherer, Lisa et al., "Recent Applications of RNAi in Mammalian Systems," *Current Pharmaceutical Biotechnology*, vol. 5:355-360 (2004).

Shah, Kavita et al., "Incorporation of an Artificial Protease and Nuclease at the HIV-1 Tat Binding Site of Trans-activation Responsive RNA," *Bioconjugate Chemistry*, vol. 7(3):283-289 (1996).

Shah, Kavita et al., "Synthesis of Uridine Phosphoramidite Analogs: Reagents for Site-Specific Incorporation of Photoreactive Sites into RNA Sequences," *Bioconjugate Chem.*, vol. 5:508-512 (1994).

Sharp, Phillip A., "RNA interference—2001," *Genes & Development*, vol. 15:485-490 (2001).

Shefner, J.M. et al., "Mice lacking cytosolic copper/zinc superoxide dismutase display a distinctive motor axonopathy," *Neurology*, vol. 53:1239-1246 (1999).

Singer, Oded et al., "Targeting BACE1 wtih siRNAs ameliorates Alzheimer disease neuropathology in a transgenic model," *Nature Neuroscience*, vol. 8(10):1343-1349 (2005).

Sioud, Mouldy et al., "Cationic liposome-mediated delivery of siRNAs in adult mice," *Biochemical and Biophysical Research Communications*, vol. 312:1220-1225 (2003).

Sisodia, Sangram S. et al., "γ-Secretase, Notch, Aβ and Alzheimer's Disease: Where do the Presenilins Fit In?" *Nature Reviews Neuroscience*, vol. 3:281-290 (2002).

Sledz, Carol A. et al., "Activation of the interferon system by short-interfering RNAs," *Nature Cell Biology*, vol. 5(9):834-839 (2003).

Song, Ji-Joon et al., "Crystal Structure of Agonaute and its Implications for RISC Slicer Activity," *Science*, vol. 305:1434-1441 (2004).

Song, Erwei et al., "Sustained Small Interfering RNA-Mediated Human Immunodeficiency Virus Type 1 Inhibition in Primary Macrophages," *Journal of Virology*, vol. 77(13):7174-7181 (2003).

Soutschek, Jürgen et al., "Therapeutic silencing of an endogenous gene by systemic administration of modified siRNAs," *Nature*, vol. 432:173-178 (2004).

Taylor, J. Paul et al., "Toxic Proteins in Neurodegenerative Disease," *Science*, vol. 296:1991-1995 (2002).

Thakker, Deepak R. et al., "Neurochemical and behavioral consequences of widespread gene knockdown in the adult mouse brain by using nonviral RNA interference," *PNAS*, vol. 101(49):17270-17275 (2004).

Tiscornia, Gustavo et al., "A general method for gene knockdown in mice by using lentiviral vectors expressing small interfering RNA," *PNAS*, vol. 100(4):1844-1848 (2003).

Tomari, Yukihide et al., "Perspective: machines for RNAi," *Genes & Development*, vol. 19:517-529 (2005).

Vella, Monica C. et al., "The *C. elegans* microRNA *let-7* binds to imperfect *let-7* complementary sites from the *lin-41* 3'UTR," *Genes & Development*, vol. 18:132-137 (2004).

Wadia, Jehangir S. et al., "Transmembrane delivery of protein and peptide drugs by TAT-mediated transduction in the treatment of cancer," *Advanced Drug Delivery Reviews*, vol. 57:579-596 (2005).

Wang, Xilu et al., "HIV-1 TAR RNA Recognition by an Unnatural Biopolymer," *J. Am. Chem. Soc.*, vol. 119:6444-6445 (1997).

Wang, Zhuying et al., "DNA damage-dependent transcriptional arrest and termination of RNA polymerase II elongation complexes in DNA template containing HIV-1 promoter," *Proc. Natl. Acad. Sci. USA*, vol. 94:6688-6693 (1997).

Wang, Zhuying et al., "Protein Orientation in the Tat-TAR Complex Determined by Psoralen Photocross-linking," *The Journal of Biological Chemistry*, vol. 271(29):16995-16998 (1996).

Wang, Zhuying et al., "RNA Conformation in the Tat-TAR Complex Determined by Site-Specific Photo-Cross-Linking," *Biochemistry*, vol. 35:6491-6499 (1996).

Wang, Zhuying et al., "RNA-Protein Interactions in the Tat-*trans*-Activation Response Element Complex Determined by Site-Specific Photo-Cross-Linking," *Biochemistry*, vol. 37:4235-4243 (1998).

Wiedau-Pazos, Martina et al., "Altered Reactivity of Superoxide Dismutase in Familial Amyotrophic Lateral Sclerosis," *Science*, vol. 271:515-518 (1996).

Wilda, Monika et al., "Killing of leukemic cells with a *BCR/ABL* fusion gene by RNA interference (RNAi)," *Oncogene*, vol. 21:5716-5724 (2002).

Williamson, Toni L. et al., "Slowing of axonal transport is a very early event in the toxicity of ALS-linked SOD1 mutants to motor neurons," *Nature Neuroscience*, vol. 2(1):50-56 (1999).

Wong, Philip C. et al., "An Adverse Property of a Familial ALS-Linked SOD1 Mutation Causes Motor Neuron Disease Characterized by Vacuolar Degeneration of Mitochondria," *Neuron*, vol. 14:1105-1116 (1995).

Wong, Philip C. et al., "Increasing Neurofilament Subunit NF-M Expression Reduces Axonal NF-H, Inhibits Radial Growth, and Results in Neurofilamentous Accumulation in Motor Neurons," *The Journal of Cell Biology*, vol. 130(6):1413-1422 (1995).

Wu, Wei-Ping et al., "Chronic lumbar catheterization of the spinal subarachnoid space in mice," *Journal of Neuroscience Methods*, vol. 133:65-69 (2004).

Xia, Haibin et al., "siRNA-mediated gene silencing in vitro and in vivo," *Nature Biotechnology*, vol. 20:1006-1010 (2002).

Xia, Xu Gang et al., "An enhanced U6 promoter for synthesis of short hairpin RNA," *Nucleic Acids Research*, vol. 31(17):1-5 (2003).

Xia, Xu-Gang et al., "Pol II-Expressed siRNA Knocks Down *Sod2* Gene Expression and Causes Phenotypes of the Gene Knockout in Mice," *PLoS Genetics*, vol. 2(1):73-80 (2006).

Yim, Hyung-Soon et al., "A Familial Amyotrophic Lateral Sclerosis-associated A4V Cu,Zn-Superoxide Dismutase Mutant Has a Lower Km for Hydrogen Peroxide," *The Journal of Biological Chemistry*, vol. 272(14):8861-8863 (1997).

Yim, Moon Bin et al., "A gain-of-function of an amyotrophic lateral sclerosis-associated Cu,Zn-superoxide dismutase mutant: An enhancement of free radical formation due to a decrease in Km for hydrogen peroxide," *Proc. Natl. Acad. Sci. USA*, vol. 93:5709-5714 (1996).

Zamore, Phillip D. et al., "Ribo-gnome: The Big World of Small RNAs," *Science*, vol. 309:1519-1524 (2005).

Zhang, Bin et al., "Neurofilaments and Orthograde Transport Are Reduced in Ventral Root Axons of Transgenic Mice that Express Human SOD1 with a G93A Mutation," *The Journal of Cell Biology*, vol. 139(5):1307-1315 (1997).

Zhang, Zhuo et al., "Antisense therapy targeting MDM2 oncogene in prostate cancer: Effects on proliferation, apoptosis, multiple gene expression, and chemotherapy," *PNAS*, vol. 100(20):11636-11641 (2003).

International Search Report for Application No. PCT/US07/02205, dated Aug. 4, 2008.

Allerson, Charles R. et al., "Fully 2'-Modified Oligonucleotide Duplexes with Improved in Vitro Potency and Stability Compared to Unmodified Small Interfering RNA," J. Med. Chem., vol. 48:901-904 (2005).

Amarzguioui, Mohammed et al., "Tolerance for mutations and chemical modifications in a siRNA," Nucleic Acids Research, vol. 31(2):589-595 (2003).

Braasch, Dwaine A. et al., "RNA Interference in Mammalian Cells by Chemically-Modified RNA," Biochemistry, vol. 42:7967-7975 (2003).

Choung, Sorim et al., "Chemical modification of siRNAs to improve serum stability without loss of efficacy," Biochemical and Biophysical Research Communications, vol. 342:919-927 (2006).

Czauderna, Frank et al., "Structural variations and stabilising modifications of synthetic siRNAs in mammalian cells," Nucleic Acids Research, vol. 31(11):2705-2716 (2003).

Harborth, Jens et al., "Sequence, Chemical, and Structural Variation of Small Interfering RNAs and Short Hairpin RNAs and the Effect on Mammalian Gene Silencing," Antisense and Nucleic Acid Drug Development, vol. 13:83-105 (2003).

Yokota, Takanori et al., "siRNA-based inhibition specific for mutant SOD1 with single nucleotide alternation in familial ALS, compared with ribozyme and DNA enzyme," Biochemical and Biophysical Research Communications, vol. 314:283-291 (2004).

Supplementary European Search Report for Application No. 07763217.2, dated Nov. 12, 2010.

* cited by examiner

Modified—nick name: R1;
Sense Strand: 21base, 41.2nmol, 7303g/mol
5' Cy3-C*G*A*2FU-G-2FU-GUCUAUUGAAG*A-2FU*2FU*C 3' (Seq. ID 5)

Antisense Strand: 21base, 45.2nmol, 6812.3g/mol
5' P-A-2FU-2FC-2FU-UCAAUAGACA-2FC-A*2FU*2FC*G*G*C 3' (Seq. ID 6)

*FIG. 1A*

Modified—Nick name: R2
Antisense Strand: 21base, 240.1nmol, 6,692.1g/mol
5' P-U-2FC-A-2FC-A-2FU-2FU-GCCCAAG-2FU-2FC-2FU-2FC*2FU*2FC*U*U 3' (Seq. ID 7)

Sense Strand: 21base, 293.2nmol, 7423.1g/mol
5' Cy3-G*G*A*GA-2FC-2FU-UGGGCAA-2FU-G-2FU*G*A*2FU*U 3' (Seq. ID 8)

*FIG. 1B*

Mismatched modified—Nick name: Mm
Antisense Strand: 21base, 405.2nmol, 6810.2g/mol
5'P-U-2'FC-A-2FC-A-2FU-2FU-GGGCAAG-2FU-G-2FU*2FC*2FC*U*U 3' (Seq. ID 9)

Sense Strand: 21base, 269.6nmol, 7305.1g/mol
5'Cy3-G*G*A*2FC-A-2FC-A-2FU-UGCCCAA-2FU-G-2FU*G*A*2FU*U 3' (Seq. ID 10)

*FIG. 1C*

Modification key: P = 5'-phosphate; 2FC = 2'fluoro-C; 2FU = 2'fluoro U; * = thiol modification at the backbone of RNA mRNA Sequence of Human SOD1 gtttggggcc agagtgggcg aggcgcggag gtctggccta taaagtagtc gcggagacgg
ggtgctggtt tgcgtcgtag tctcctgcag cgtctgggt ttccgttgca gtcctcggaa
ccaggacctc ggcgtggcct agcgagttat ggcgacgaag gccgtgtgcg tgctgaaggg
cgacggccca gtgcagggca tcatcaattt cgagcagaag gaaagtaatg gaccagtgaa
ggtgtgggga agcattaaag gactgactga aggcctgcat ggattccatg ttcatgagtt
tggagataat acagcaggct gtaccagtgc aggtcctcac tttaatcctc tatccagaaa
acacggtggg ccaaaggatg aagagaggca tgttggagac ttggcaatg tgactgctga
caaagatggt gtggccgatg tgtctattga agattctgtg atctcactct caggagacca
ttgcatcatt ggccgcacac tggtggtcca tgaaaaagca gatgactgg ttggcttgtg gtgtaattgg
aaatgaagaa agtacaaaga caggaaaacgc tggaagtcgt ttggcttgtg gtgtaattgg
gatcgcccaa taaacattcc cttgatgta gtctgaggcc ccttaactca tctgttatcc
tgctagctgt agaaatgtat cctgataaac attaaacact gtaatcttaa aagtgtaatt
gtgtgacttt ttcagagttg cttaaagta cctgtagta gaaactgatt tatgatcact
tggaagattt gtatagtttt ataaaactca gttaaaatgt ctgtttcaat gacctgtatt
ttgccagact taaatcacag atgggtatta aacttgtcag aattcttttg tcattcaagc
ctgtgaataa aaaccctgta tggcacttat tatgaggcta ttaaaagaat ccaaattcaa
actaaaaaaa aaaaaaaaa a (Seq. ID 11)

*FIG. 8*

SEQUENCE LISTING

<160> NUMBER OF SEQ ID NOS: 11

<210> SEQ ID NO 1
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: 2'fluorouricil
<220> FEATURE:
<221> NAME/KEY: modified_base
<222> LOCATION: (18)
<223> OTHER INFORMATION: 2'fluorouricil
<220> FEATURE:
<221> NAME/KEY: modified_base
<222> LOCATION: (21)
<223> OTHER INFORMATION: 2'fluorocytidine
<220> FEATURE:
<221> NAME/KEY: misc_feature
<222> LOCATION: (21)..(22)
<223> OTHER INFORMATION: Phosphorothioate backbone linkage
<220> FEATURE:
<221> NAME/KEY: misc_feature
<222> LOCATION: (22)..(23)
<223> OTHER INFORMATION: Phosphorothioate backbone linkage

<400> SEQUENCE: 1
anngguauuc aguguganga nac                                        23

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate backbone linkage
<220> FEATURE:
<221> NAME/KEY: modified_base
<222> LOCATION: (2)
<223> OTHER INFORMATION: 2'fluorouricil
<220> FEATURE:
<221> NAME/KEY: modified_base
<222> LOCATION: (3)
<223> OTHER INFORMATION: 2'fluorocytidine
<220> FEATURE:
<221> NAME/KEY: modified_base
<222> LOCATION: (5)
<223> OTHER INFORMATION: 2'fluorouricil
<220> FEATURE:
<221> NAME/KEY: modified_base
<222> LOCATION: (6)
<223> OTHER INFORMATION: 2'fluorocytidine
<220> FEATURE:
<221> NAME/KEY: modified_base
<222> LOCATION: (17)..(18)
<223> OTHER INFORMATION: 2'fluorocytidine
<220> FEATURE:
<221> NAME/KEY: misc_feature
<222> LOCATION: (20)..(21)
<223> OTHER INFORMATION: Phosphorothioate backbone linkage
<220> FEATURE:
<221> NAME/KEY: modified_base
<222> LOCATION: (21)
<223> OTHER INFORMATION: 2'fluorouricil

<400> SEQUENCE: 2
gnnannacac ugaauannaa n    21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 2'fluorouricil
<220> FEATURE:
<221> NAME/KEY: modified_base
<222> LOCATION: (5)
<223> OTHER INFORMATION: 2'fluorouricil
<220> FEATURE:
<221> NAME/KEY: modified_base
<222> LOCATION: (6)
<223> OTHER INFORMATION: 2'fluorocytidine
<220> FEATURE:
<221> NAME/KEY: modified_base
<222> LOCATION: (17)
<223> OTHER INFORMATION: 2'fluorocytidine
<220> FEATURE:
<221> NAME/KEY: misc_feature
<222> LOCATION: (20)..(21)
<223> OTHER INFORMATION: Phosphorothioate backbone linkage
<220> FEATURE:
<221> NAME/KEY: modified_base
<222> LOCATION: (21)
<223> OTHER INFORMATION: 2'fluorouricil

<400> SEQUENCE: 3
gngannagac ucaauangaa n    21

<210> SEQ ID NO 4
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: 2'fluorouricil
<220> FEATURE:
<221> NAME/KEY: modified_base
<222> LOCATION: (18)
<223> OTHER INFORMATION: 2'fluorouricil
<220> FEATURE:
<221> NAME/KEY: modified_base
<222> LOCATION: (21)
<223> OTHER INFORMATION: 2'fluorocytidine
<220> FEATURE:
<221> NAME/KEY: misc_feature
<222> LOCATION: (21)..(22)
<223> OTHER INFORMATION: Phosphorothioate backbone linkage
<220> FEATURE:
<221> NAME/KEY: misc_feature
<222> LOCATION: (22)..(23)
<223> OTHER INFORMATION: Phosphorothioate backbone linkage

<400> SEQUENCE: 4
anncguauug agucuganca nac    23

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: misc_feature
<222> LOCATION: (1)..(2)
<223> OTHER INFORMATION: Thiol modification at the backbone of RNA
<220> FEATURE:
<221> NAME/KEY: misc_feature
<222> LOCATION: (2)..(3)
<223> OTHER INFORMATION: Thiol modification at the backbone of RNA
<220> FEATURE:
<221> NAME/KEY: misc_feature
<222> LOCATION: (3)..(4)
<223> OTHER INFORMATION: Thiol modification at the backbone of RNA
<220> FEATURE:
<221> NAME/KEY: modified_base
<222> LOCATION: (4)
<223> OTHER INFORMATION: 2'fluorouricil
<220> FEATURE:
<221> NAME/KEY: modified_base
<222> LOCATION: (6)
<223> OTHER INFORMATION: 2'fluorouricil
<220> FEATURE:
<221> NAME/KEY: misc_feature
<222> LOCATION: (17)..(18)
<223> OTHER INFORMATION: Thiol modification at the backbone of RNA
<220> FEATURE:
<221> NAME/KEY: modified_base
<222> LOCATION: (19)..(20)
<223> OTHER INFORMATION: 2'fluorouricil
<220> FEATURE:
<221> NAME/KEY: misc_feature
<222> LOCATION: (19)..(20)
<223> OTHER INFORMATION: Thiol modification at the backbone of RNA
<220> FEATURE:
<221> NAME/KEY: misc_feature
<222> LOCATION: (20)..(21)
<223> OTHER INFORMATION: Thiol modification at the backbone of RNA

<400> SEQUENCE: 5
cgangngucu auugaagann c                                            21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(4)
<223> OTHER INFORMATION: 2'fluorouricil
<220> FEATURE:
<221> NAME/KEY: modified_base
<222> LOCATION: (15)
<223> OTHER INFORMATION: 2'fluorocytidine
<220> FEATURE:
<221> NAME/KEY: misc_feature
<222> LOCATION: (16)..(17)
<223> OTHER INFORMATION: Thiol modification at the backbone of RNA
<220> FEATURE:
<221> NAME/KEY: modified_base
<222> LOCATION: (17)
<223> OTHER INFORMATION: 2'fluorouricil
<220> FEATURE:
<221> NAME/KEY: misc_feature
<222> LOCATION: (17)..(18)
<223> OTHER INFORMATION: Thiol modification at the backbone of RNA
<220> FEATURE:
<221> NAME/KEY: modified_base
<222> LOCATION: (18)
<223> OTHER INFORMATION: 2'fluorocytidine
<220> FEATURE:
<221> NAME/KEY: misc_feature
<222> LOCATION: (18)..(19)
<223> OTHER INFORMATION: Thiol modification at the backbone of RNA
<220> FEATURE:
<221> NAME/KEY: misc_feature
<222> LOCATION: (19)..(20)
```

```
<223> OTHER INFORMATION: Thiol modification at the backbone of RNA
<220> FEATURE:
<221> NAME/KEY: misc_feature
<222> LOCATION: (20)..(21)
<223> OTHER INFORMATION: Thiol modification at the backbone of RNA

<400> SEQUENCE: 6
annnucaaua gacananngg c                                              21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 2'fluorocytidine
<220> FEATURE:
<221> NAME/KEY: modified_base
<222> LOCATION: (4)
<223> OTHER INFORMATION: 2'fluorocytidine
<220> FEATURE:
<221> NAME/KEY: modified_base
<222> LOCATION: (6)..(7)
<223> OTHER INFORMATION: 2'fluorouricil
<220> FEATURE:
<221> NAME/KEY: modified_base
<222> LOCATION: (15)
<223> OTHER INFORMATION: 2'fluorouricil
<220> FEATURE:
<221> NAME/KEY: modified_base
<222> LOCATION: (16)
<223> OTHER INFORMATION: 2'fluorocytidine
<220> FEATURE:
<221> NAME/KEY: modified_base
<222> LOCATION: (17)
<223> OTHER INFORMATION: 2'fluorouricil
<220> FEATURE:
<221> NAME/KEY: misc_feature
<222> LOCATION: (17)..(18)
<223> OTHER INFORMATION: Thiol modification at the backbone of RNA
<220> FEATURE:
<221> NAME/KEY: modified_base
<222> LOCATION: (18)..(19)
<223> OTHER INFORMATION: 2'fluorocytidine
<220> FEATURE:
<221> NAME/KEY: misc_feature
<222> LOCATION: (18)..(19)
<223> OTHER INFORMATION: Thiol modification at the backbone of RNA
<220> FEATURE:
<221> NAME/KEY: misc_feature
<222> LOCATION: (19)..(20)
<223> OTHER INFORMATION: Thiol modification at the backbone of RNA
<220> FEATURE:
<221> NAME/KEY: misc_feature
<222> LOCATION: (20)..(21)
<223> OTHER INFORMATION: Thiol modification at the backbone of RNA

<400> SEQUENCE: 7
unananngcc caagnnnnnu u                                              21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Thiol modification at the backbone of RNA
<220> FEATURE:
```

```
<221> NAME/KEY: misc_feature
<222> LOCATION: (2)..(3)
<223> OTHER INFORMATION: Thiol modification at the backbone of RNA
<220> FEATURE:
<221> NAME/KEY: misc_feature
<222> LOCATION: (3)..(4)
<223> OTHER INFORMATION: Thiol modification at the backbone of RNA
<220> FEATURE:
<221> NAME/KEY: modified_base
<222> LOCATION: (6)
<223> OTHER INFORMATION: 2'fluorocytidine
<220> FEATURE:
<221> NAME/KEY: modified_base
<222> LOCATION: (7)
<223> OTHER INFORMATION: 2'fluorouricil
<220> FEATURE:
<221> NAME/KEY: modified_base
<222> LOCATION: (15)
<223> OTHER INFORMATION: 2'fluorouricil
<220> FEATURE:
<221> NAME/KEY: modified_base
<222> LOCATION: (17)
<223> OTHER INFORMATION: 2'fluorouricil
<220> FEATURE:
<221> NAME/KEY: misc_feature
<222> LOCATION: (17)..(18)
<223> OTHER INFORMATION: Thiol modification at the backbone of RNA
<220> FEATURE:
<221> NAME/KEY: misc_feature
<222> LOCATION: (18)..(19)
<223> OTHER INFORMATION: Thiol modification at the backbone of RNA
<220> FEATURE:
<221> NAME/KEY: misc_feature
<222> LOCATION: (19)..(20)
<223> OTHER INFORMATION: Thiol modification at the backbone of RNA
<220> FEATURE:
<221> NAME/KEY: modified_base
<222> LOCATION: (20)
<223> OTHER INFORMATION: 2'fluorouricil
<220> FEATURE:
<221> NAME/KEY: misc_feature
<222> LOCATION: (20)..(21)
<223> OTHER INFORMATION: Thiol modification at the backbone of RNA

<400> SEQUENCE: 8
ggagannugg gcaangngan u                                              21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 2'fluorocytidine
<220> FEATURE:
<221> NAME/KEY: modified_base
<222> LOCATION: (4)
<223> OTHER INFORMATION: 2'fluorocytidine
<220> FEATURE:
<221> NAME/KEY: modified_base
<222> LOCATION: (6)..(7)
<223> OTHER INFORMATION: 2'fluorouricil
<220> FEATURE:
<221> NAME/KEY: modified_base
<222> LOCATION: (15)
<223> OTHER INFORMATION: 2'fluorouricil
<220> FEATURE:
<221> NAME/KEY: modified_base
<222> LOCATION: (17)
<223> OTHER INFORMATION: 2'fluorouricil
<220> FEATURE:
<221> NAME/KEY: misc_feature
<222> LOCATION: (17)..(18)
<223> OTHER INFORMATION: Thiol modification at the backbone of RNA
```

```
<220> FEATURE:
<221> NAME/KEY: modified_base
<222> LOCATION: (18)..(19)
<223> OTHER INFORMATION: 2'fluorouricil
<220> FEATURE:
<221> NAME/KEY: misc_feature
<222> LOCATION: (18)..(19)
<223> OTHER INFORMATION: Thiol modification at the backbone of RNA
<220> FEATURE:
<221> NAME/KEY: misc_feature
<222> LOCATION: (19)..(20)
<223> OTHER INFORMATION: Thiol modification at the backbone of RNA
<220> FEATURE:
<221> NAME/KEY: misc_feature
<222> LOCATION: (20)..(21)
<223> OTHER INFORMATION: Thiol modification at the backbone of RNA

<400> SEQUENCE: 9 unananggg caagngnnnu u                                                    21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Thiol modification at the backbone of RNA
<220> FEATURE:
<221> NAME/KEY: misc_feature
<222> LOCATION: (2)..(3)
<223> OTHER INFORMATION: Thiol modification at the backbone of RNA
<220> FEATURE:
<221> NAME/KEY: misc_feature
<222> LOCATION: (3)..(4)
<223> OTHER INFORMATION: Thiol modification at the backbone of RNA
<220> FEATURE:
<221> NAME/KEY: modified_base
<222> LOCATION: (4)
<223> OTHER INFORMATION: 2'fluorocytidine
<220> FEATURE:
<221> NAME/KEY: modified_base
<222> LOCATION: (6)
<223> OTHER INFORMATION: 2'fluorocytidine
<220> FEATURE:
<221> NAME/KEY: modified_base
<222> LOCATION: (7)
<223> OTHER INFORMATION: 2'fluorouricil
<220> FEATURE:
<221> NAME/KEY: modified_base
<222> LOCATION: (15)
<223> OTHER INFORMATION: 2'fluorouricil
<220> FEATURE:
<221> NAME/KEY: modified_base
<222> LOCATION: (17)
<223> OTHER INFORMATION: 2'fluorouricil
<220> FEATURE:
<221> NAME/KEY: misc_feature
<222> LOCATION: (17)..(18)
<223> OTHER INFORMATION: Thiol modification at the backbone of RNA
<220> FEATURE:
<221> NAME/KEY: misc_feature
<222> LOCATION: (18)..(19)
<223> OTHER INFORMATION: Thiol modification at the backbone of RNA
<220> FEATURE:
<221> NAME/KEY: misc_feature
<222> LOCATION: (19)..(20)
<223> OTHER INFORMATION: Thiol modification at the backbone of RNA
<220> FEATURE:
<221> NAME/KEY: modified_base
<222> LOCATION: (20)
<223> OTHER INFORMATION: 2'fluorouricil
<220> FEATURE:
<221> NAME/KEY: misc_feature
<222> LOCATION: (20)..(21)
```

```
<223> OTHER INFORMATION: Thiol modification at the backbone of RNA

<400> SEQUENCE: 10
gganannugc ccaangngan u                                              21

<210> SEQ ID NO 11
<211> LENGTH: 981
<212> TYPE: DNA
<213> ORGANISM: Homo sapiens

<400> SEQUENCE: 11
gtttggggcc agagtgggcg aggcgcggag gtctggccta taaagtagtc gcggagacgg     60
ggtgctggtt tgcgtcgtag tctcctgcag cgtctggggt ttccgttgca gtcctcggaa    120
ccaggacctc ggcgtggcct agcgagttat ggcgacgaag gccgtgtgcg tgctgaaggg    180
cgacggccca gtgcagggca tcatcaattt cgagcagaag gaaagtaatg gaccagtgaa    240
ggtgtgggga agcattaaag gactgactga aggcctgcat ggattccatg ttcatgagtt    300
tggagataat acagcaggct gtaccagtgc aggtcctcac tttaatcctc tatccagaaa    360
acacggtggg ccaaaggatg aagagaggca tgttggagac ttgggcaatg tgactgctga    420
caaagatggt gtggccgatg tgtctattga agattctgtg atctcactct caggagacca    480
ttgcatcatt ggccgcacac tggtggtcca tgaaaaagca gatgacttgg gcaaaggtgg    540
aaatgaagaa agtacaaaga caggaaacgc tggaagtcgt ttggcttgtg gtgtaattgg    600
gatcgcccaa taaacattcc cttggatgta gtctgaggcc ccttaactca tctgttatcc    660
tgctagctgt agaaatgtat cctgataaac attaaacact gtaatcttaa aagtgtaatt    720
gtgtgacttt ttcagagttg ctttaaagta cctgtagtga gaaactgatt tatgatcact    780
tggaagattt gtatagtttt ataaaactca gttaaaatgt ctgtttcaat gacctgtatt    840
ttgccagact taaatcacag atgggtatta aacttgtcag aatttctttg tcattcaagc    900
ctgtgaataa aaaccctgta tggcacttat tatgaggcta ttaaaagaat ccaaattcaa    960
actaaaaaaa aaaaaaaaa a                                              981
```

RNA INTERFERENCE AGENTS FOR THERAPEUTIC USE

RELATED APPLICATIONS

This application claims priority to and the benefit of U.S. Ser. No. 60/762,957, entitled "RNA Interference Agents for Use in Therapy," filed on Jan. 26, 2006; U.S. Ser. No. 60/762,956, entitled "Nanotransporters for Efficient Delivery of Nucleic Acid and Other Pharmaceutical Agents," filed on Jan. 26, 2006; and U.S. Ser. No. 60/762,951, entitled "RNA Interference Agents for Use in Therapy of Metabolic Disorders," filed on Jan. 26, 2006. The entire contents of these applications are hereby incorporated herein by reference.

BACKGROUND OF THE INVENTION

RNA interference (RNAi) is the process whereby double-stranded RNA (dsRNA) induces the sequence-specific degradation of homologous mRNA. Although RNAi was first discovered in *Caenorhabditis elegans* (Fire et al., 1998), similar phenomena had been reported in plants (post-transcriptional gene silencing [PTGS]) and in *Neurospora crassa* (quelling) (reviewed in Hammond et al., 2001; Sharp, 2001). It has become clear that dsRNA-induced silencing phenomena are present in evolutionarily diverse organisms, e.g., nematodes, plants, fungi and trypanosomes (Bass, 2000; Cogoni and Macino, 2000; Fire et al., 1998; Hammond et al., 2001; Ketting and Plasterk, 2000; Matzke et al., 2001; Sharp, 2001; Sijen and Kooter, 2000; Tuschl, 2001; Waterhouse et al., 2001). Biochemical studies in *Drosophila* embryo lysates and S2 cell extracts have begun to unravel the mechanisms by which RNAi works (Bernstein et al., 2001; Tuschl et al., 1999; Zamore et al., 2000).

Although work has been done generally in the area of RNAi, there is a need for further study of such systems. Moreover, there exists a need for the development of reagents suitable for use in vivo, in particular for use in developing human therapeutics.

SUMMARY OF THE INVENTION

The present invention is based on the discovery that chemically modified siRNA molecules (e.g., siRNA molecules modified at both the 3' and the 5' end of both the sense strand and the antisense strand) can be used in human therapeutic applications, and are improved without compromising the RNAi activity of the siRNA molecules.

Accordingly, in one aspect the present invention is directed to a small interfering RNA (siRNA), which includes a sense strand and an antisense strand, each having a 5' end a 3' end. Generally the antisense strand has a sequence sufficiently complementary to a target mRNA sequence to direct target-specific RNA interference (RNAi). In some aspects, the sense strand or antisense strand is modified at both the 5' end and the 3' end with a chemically modified nucleotide, such that in vivo stability is enhanced as compared to a corresponding unmodified siRNA. In some aspects, the sense strand or antisense strand is modified at both the 5' end and the 3' end with one or more chemically modified nucleotides, such that the target efficiency is enhanced compared to a corresponding unmodified siRNA. In some embodiments, the sense strand or antisense strand is modified at both the 5' end and the 3' end with one or more chemically modified nucleotides, and the antisense strand is capable of adopting an A-form helix when in association with a target RNA. In some embodiments, the sense strand or antisense strand is modified at both the 5' end and the 3' end with one or more chemically modified nucleotides, and the antisense strand is capable of adopting an A-form helix having a normal major groove when in association with a target RNA.

In some embodiments, both the sense strand and the antisense strand are modified at both the 3' end and the 5' end with one or more chemically modified nucleotide. In some embodiments, the siRNA is sufficiently complementary to a target mRNA, said target mRNA specifying the amino acid sequence of a cellular protein. In some embodiments, the siRNA is sufficiently complementary to a target mRNA, said target mRNA specifying the amino acid sequence of a viral protein.

In some embodiments, the siRNA of the present invention includes a sense strand and an antisense strand each according to formula IV:

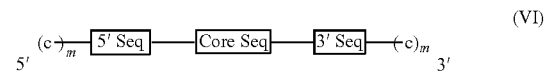

(VI)

wherein each occurrence of c is independently an end modification; each occurrence of m is an integer of 0 or 1;
-5'Seq- and -3'Seq- each independently comprise 2-10 nucleotides, wherein the nucleotides are purine and pyrimidine nucleotides, wherein about 1-6 nucleotides are modified and wherein each internucleotide linkage in the unit is optionally modified;
-CoreSeq- comprises 5-20 unmodified nucleotides linked via phosphate internucleotide linkages; and
-5'Seq- is linked to -CoreSeq- via an optionally modified internucleotide linkage and -CoreSeq- is linked to -3'Seq- via an optionally modified internucleotide linkage.

In some embodiments, -5'Seq- is represented by the formula:

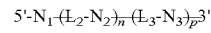

wherein n is an integer from 2-9; p is an integer from 0-3; $N_1$ is an unmodified nucleotide;
each occurrence of $N_2$ is independently selected from the group consisting of a modified purine nucleotide, an unmodified purine nucleotide and a modified pyrimidine nucleotide, wherein about 1-6 occurrences of $N_2$ are modified pyrimidine nucleotides; each occurrence of $N_3$ is independently selected from the group consisting of a modified purine nucleotide, an unmodified purine nucleotide, a modified pyrimidine nucleotide and an unmodified pyrimidine nucleotide; and
each occurrence of $L_2$ and $L_3$ are independently a phosphate linkage or a linkage according to formula III.

In some embodiments, -CoreSeq- is represented by the formula:

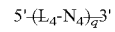

wherein q is an integer from 5-15; each occurrence of $N_4$ is an unmodified nucleotide; and each occurrence of $L_4$ is independently a phosphate linkage.

In some embodiments, -3'Seq- is represented by the formula:

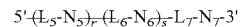

wherein:
r is an integer from 3-9; s is an integer from 0 to 3; $N_7$ is an unmodified nucleotide;
each occurrence of $N_5$ is independently selected from the group consisting of a modified purine nucleotide, an unmodified purine nucleotide and a modified pyrimidine nucleotide, wherein about 1-6 occurrences of $N_5$ are modified pyrimidine nucleotides;

each occurrence of $N_6$ is independently selected from the group consisting of a modified purine nucleotide, an unmodified purine nucleotide, a modified pyrimidine nucleotide and an unmodified pyrimidine nucleotide;

each occurrence of $L_5$ and $L_6$ are independently a phosphate linkage or a linkage according to formula III;

and $L_7$ is a linkage according to formula III.

In some embodiments, the modified nucleotide is a sugar-modified nucleotide. Sugar modified nucleotides include, but are not limited to 2'-fluoro, 2'-amino and 2'-thio modified ribonucleotides, e.g. 2'-fluoro modified ribonucleotides. In some embodiments, the 2'-fluoro ribonucleotides are in both the sense and antisense strands. In some embodiments, the 2'-fluoro modified ribonucleotide is 2'-fluoro uridine or 2'-fluoro cytidine. In some embodiments, the modified nucleotide is a 2'-deoxy ribonucleotide, e.g., 2'-deoxy adenosine or 2'-deoxy guanosine.

In some embodiments, the modified nucleotide is a nucleobase-modified nucleotide.

In some embodiments, the modified nucleotide is a backbone-modified nucleotide, e.g., a phosphorothioate group. In some embodiments, the backbone-modified nucleotide contains a phosphorothioate group and is present within the sense and antisense strands.

In some embodiments, the antisense strand and target mRNA sequences are 100% complementary. In other embodiments, the antisense strand and target mRNA sequences comprise at least one mismatch.

In some embodiments, the chemically modified nucleotide does not effect the ability of the antisense strand to adopt A-form helix conformation when base-pairing with the target mRNA sequence. In some embodiments, the modified nucleotide does not effect the ability of the antisense strand to adopt A-form helix conformation comprising a normal major groove when base-pairing with the target mRNA sequence.

The siRNA can be between about 10 and 50 residues in length, e.g., between about 18 and 25 residues in length. In some embodiments, the siRNA is chemically synthesized.

The present invention also includes transgenes that encode any of the siRNAs described herein and compositions comprising any of the siRNAs described herein and a pharmaceutically acceptable carrier.

In some aspects, the present invention includes a method of activating target-specific RNA interference (RNAi) in a cell, the method including introducing into said cell any of the siRNA described herein in an amount sufficient for degradation of target mRNA to occur, thereby activating target-specific RNAi in the cell.

In some embodiments, the siRNA is introduced into the cell by contacting the cell with the siRNA. In some embodiments, the siRNA is introduced into the cell by contacting the cell with a composition comprising the siRNA and a lipophilic carrier. In some embodiments, the siRNA is introduced into the cell by transfecting or infecting the cell with a vector comprising nucleic acid sequences capable of producing the siRNA when transcribed in the cell. In some embodiments, the siRNA is introduced into the cell by injecting into the cell a vector comprising nucleic acid sequences capable of producing the siRNA when transcribed in the cell. The vector can include transgene nucleic acid sequences.

In still other aspects, the present invention includes a method of activating target-specific RNA interference (RNAi) in an organism. The method generally includes administering to said organism any of the siRNAs described herein in an amount sufficient for degradation of the target mRNA to occur, thereby activating target-specific RNAi in the organism. In some embodiments, the siRNA is administered by an intravenous or intraperitoneal route.

The present invention is also directed to cells and organism obtained by the methods of the present invention, including but not limited to cells of mammalian origin, cells of murine origin, cells of human origin, embryonic stem cells, organisms of mammalian origin, organisms of murine origin, and organisms of human origin.

In some embodiments, degradation of the target mRNA produces a loss-of-function phenotype. In some embodiments, degradation of the target mRNA is such that the protein specified by said target mRNA is decreased by at least about 10% or at least about 20%.

In some aspects, the present invention includes a method of treating a disease or disorder associated with the activity of a protein specified by a target mRNA in a subject. The method includes administering to the subject any of the siRNAs described herein in an amount sufficient for degradation of the target mRNA to occur, thereby treating the disease or disorder associated with the protein. In some embodiments, the disease or disorder is ALS.

In some embodiments, the target mRNA specifies the amino acid sequence of a protein involved or predicted to be involved in a human disease or disorder. In some embodiments, the target mRNA is a SOD1 mRNA. SOD1 mRNAs include a wild type SOD1 mRNA, a mutant SOD1 mRNA, e.g., a G93A SOD1 or both mutant and wild type SOD1 mRNA.

The present invention also includes kits that generally include any of the siRNA molecules described herein and instructions for use for activating target-specific RNA interference (RNAi) in a cell or organism.

BRIEF DESCRIPTION OF THE DRAWINGS

FIG. 1 depicts exemplary terminally-modified siRNAs directed to SOD1, termed R1 (FIG. 1A), R2 (FIG. 1B) and Mm (FIG. 1C).

FIG. 8 depicts the mRNA sequence of human SOD1.

DETAILED DESCRIPTION OF THE INVENTION

Figure 2:
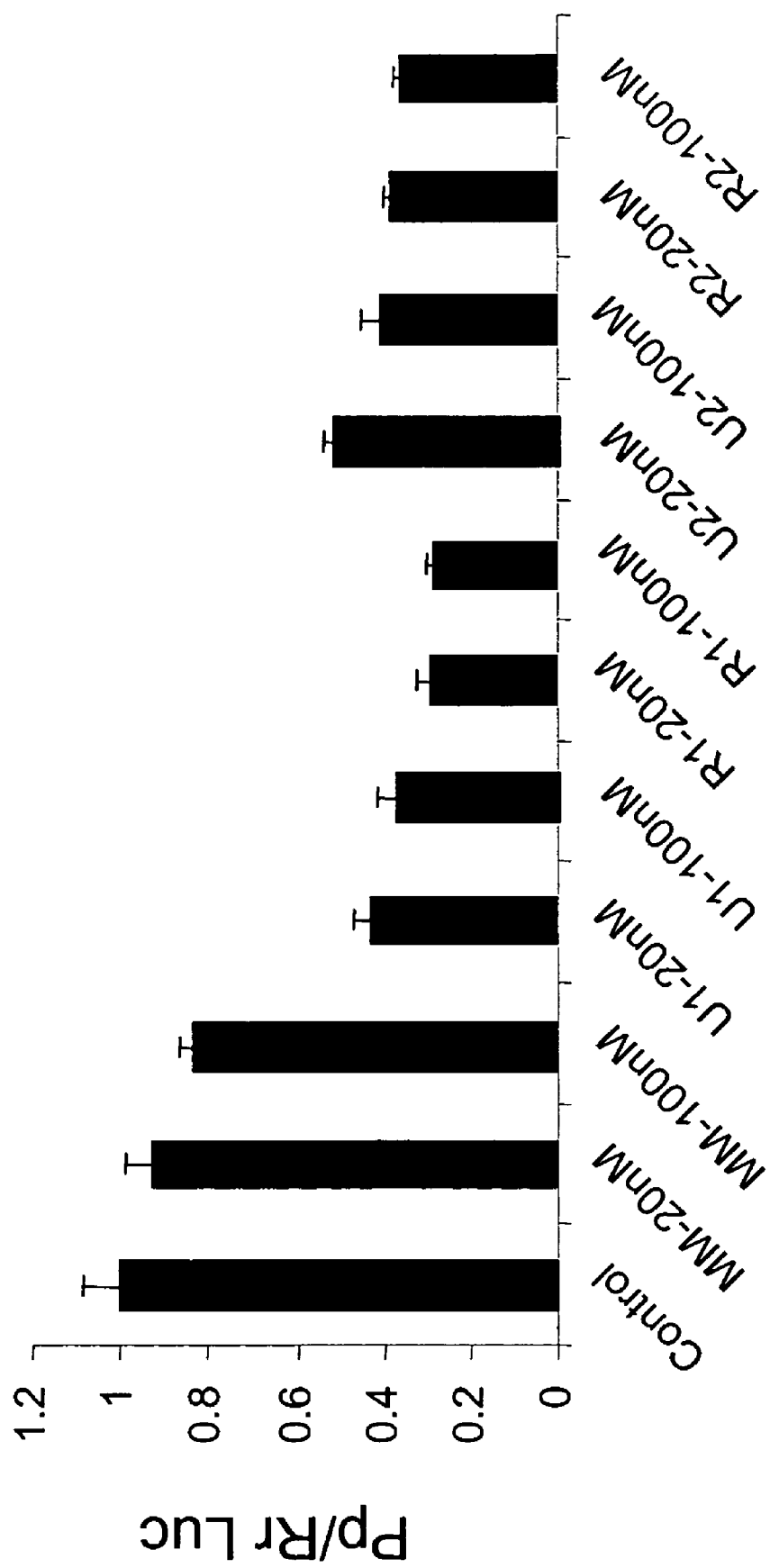
FIG. 2 depicts silencing efficiency of terminally-modified siRNAs as compared to their corresponding unmodified siRNAs in host cells using the dual luciferase assay. R1, R2 and MM refer to the modified siRNAs in FIG. 1. U1 and U2 refer to unmodified siRNAs corresponding to R1 and R2, respectively.

The present invention features chemically modified RNAi agents, e.g., small interfering RNA molecules (siRNA), and methods (e.g., research and/or therapeutic methods) for using said siRNA molecules. Specifically, the present invention includes RNAi agents which have been chemically modified at both the 3' end and the 5' end of the sense strand, the antisense strand or both. Such chemically modified siRNAs are useful, for example, in knockdown therapy, e.g., to knock down the function of mutant SOD1 mRNA.

So that the invention may be more readily understood, certain terms are first defined:

It is to be noted that the singular forms "a," "an," and "the" as used herein include "at least one" and "one or more" unless stated otherwise. Thus, for example, reference to "a pharmacologically acceptable carrier" includes mixtures of two or more carriers as well as a single carrier, and the like.

As used herein, the term "RNA silencing" refers to a group of sequence-specific regulatory mechanisms (e.g. RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding protein-coding gene. RNA silencing has been observed in many types of organisms, including plants, animals, and fungi.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence", e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g. promoter or enhancer elements) of a target gene. In other embodiments, the target polynucleotide sequence is a target mRNA encoded by a target gene.

As used herein, the term "target gene" is a gene whose expression is to be substantially inhibited or "silenced." This silencing can be achieved by RNA silencing, e.g. by cleaving the mRNA of the target gene or translational repression of the target gene. The term "non-target gene" is a gene whose expression is not to be substantially inhibited. In one embodiment, the polynucleotide sequences of the target and non-target gene (e.g. mRNA encoded by the target and non-target genes) can differ by one or more nucleotides. In another embodiment, the target and non-target genes can differ by one or more polymorphisms. In another embodiment, the target and non-target genes can share less than 100% sequence identity. In another embodiment, the non-target gene may be a homolog (e.g. an ortholog or paralog) of the target gene.

A "target allele" is an allele whose expression is to be selectively inhibited or "silenced." This silencing can be achieved by RNA silencing, e.g. by cleaving the mRNA of the target gene or target allele by an siRNA. The term "non-target allele" is a allele whose expression is not to be substantially inhibited. In certain embodiments, the target and non-target alleles can correspond to the same target gene. In other embodiments, the target allele corresponds to a target gene, and the non-target allele corresponds to a non-target gene. In one embodiment, the polynucleotide sequences of the target and non-target alleles can differ by one or more nucleotides. In another embodiment, the target and non-target alleles can differ by one or more allelic polymorphisms. In another embodiment, the target and non-target alleles can share less than 100% sequence identity.

The term "polymorphism" as used herein, refers to a variation (e.g., a deletion, insertion, or substitution) in a gene sequence that is identified or detected when the same gene sequence from different sources or subjects (but from the same organism) are compared. For example, a polymorphism can be identified when the same gene sequence from different subjects (but from the same organism) are compared. Identification of such polymorphisms is routine in the art, the methodologies being similar to those used to detect, for example, breast cancer point mutations. Identification can be made, for example, from DNA extracted from a subject's lymphocytes, followed by amplification of polymorphic regions using specific primers to said polymorphic region. Alternatively, the polymorphism can be identified when two alleles of the same gene are compared.

A variation in sequence between two alleles of the same gene within an organism is referred to herein as an "allelic polymorphism". The polymorphism can be at a nucleotide within a coding region but, due to the degeneracy of the genetic code, no change in amino acid sequence is encoded. Alternatively, polymorphic sequences can encode a different amino acid at a particular position, but the change in the amino acid does not affect protein function. Polymorphic regions can also be found in non-encoding regions of the gene.

As used herein, the term "RNA silencing agent" refers to an RNA which is capable of inhibiting or "silencing" the expression of a target gene. In certain embodiments, the RNA silencing agent is capable of preventing complete processing (e.g, the full translation and/or expression) of a mRNA molecule through a post-transcriptional silencing mechanism. RNA silencing agents include small (<50 b.p.), noncoding RNA molecules, for example RNA duplexes comprising paired strands, as well as precursor RNAs from which such small non-coding RNAs can be generated. Exemplary RNA silencing agents include siRNAs, miRNAs, siRNA-like duplexes, and dual-function oligonucleotides as well as precursors thereof. In one embodiment, the RNA silencing agent is capable of inducing RNA interference. In another embodiment, the RNA silencing agent is capable of mediating translational repression.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, $^2$N-methylguanosine and $^{2,2}$N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "rare nucleotide" refers to a naturally occurring nucleotide that occurs infrequently, including naturally occurring deoxyribonucleotides or ribonucleotides that occur infrequently, e.g., a naturally occurring ribonucleotide that is not guanosine, adenosine, cytosine, or uridine. Examples of rare nucleotides include, but are not limited to, inosine, 1-methyl inosine, pseudouridine, 5,6-dihydrouridine, ribothymidine, $^2$N-methylguanosine and $^{2,2}$N,N-dimethylguanosine.

The term "nucleotide analog" or "altered nucleotide" or "modified nucleotide" refers to a non-standard nucleotide, including non-naturally occurring ribonucleotides or deoxyribonucleotides. Similarly, the term "unmodified nucleotide" is used interchangeably herein with the term "naturally occurring nucleotide." Preferred nucleotide analogs are modified at any position so as to alter certain chemical properties of the nucleotide yet retain the ability of the nucleotide analog to perform its intended function. Examples of preferred modified nucleotides include, but are not limited to, 2-amino-guanosine, 2-amino-adenosine, 2,6-diamino-guanosine and 2,6-diamino-adenosine. Examples of positions of the nucleotide which may be derivitized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, *Antisense Nucleic Acid Drug Dev.*, 2000 Aug. 10(4):297-310.

Nucleotide analogs may also comprise modifications to the sugar portion of the nucleotides. For example the 2' OH- group may be replaced by a group selected from H, OR, R, F, Cl, Br, I, SH, SR, NH$_2$, NHR, NR$_2$, COOR, or OR, wherein R is substituted or unsubstituted C$_1$-C$_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, *Antisense Nucleic Acid Drug Dev.* 2000 Apr. 10(2):117-21, Rusckowski et al. *Antisense Nucleic Acid Drug Dev.* 2000 Oct. 10(5):333-45, Stein, *Antisense Nucleic Acid Drug Dev.* 2001 Oct. 11(5): 317-25, Vorobjev et al. *Antisense Nucleic Acid Drug Dev.* 2001 Apr. 11(2):77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

The term "oligonucleotide" refers to a short polymer of nucleotides and/or nucleotide analogs. The term "RNA analog" refers to a polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. The oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, and/or phosphorothioate linkages. Exemplary RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA silencing (e.g. RNA interference). In an exemplary embodiment, oligonucleotides comprise Locked Nucleic Acids (LNAs) or Peptide Nucleic Acids (PNAs).

As used herein, the term "bond strength" or "base pair strength" refers to the strength of the interaction between pairs of nucleotides (or nucleotide analogs) on opposing strands of an oligonucleotide duplex (e.g., a duplex formed by a strand of a RNA silencing agent and a target mRNA sequence), due primarily to H-bonding, Van der Waals interactions, and the like between said nucleotides (or nucleotide analogs).

As used here, the term "melting temperature" or "Tm" refers to the temperature at which half of a population of double-stranded polynucleotide molecules becomes dissociated into single strands.

As used herein, the terms "sufficient complementarity" or "sufficient degree of complementarity" mean that the RNA silencing agent has a sequence (e.g. in the antisense strand, mRNA targeting moiety or miRNA recruiting moiety) which is sufficient to bind the desired target RNA, respectively, and to trigger the RNA silencing of the target mRNA.

As used herein, the term "RNA interference" ("RNAi") refers to a type of RNA silencing which results in the selective intracellular degradation of a target RNA. RNAi occurs in cells naturally to remove foreign RNAs (e.g., viral RNAs). Natural RNAi proceeds via fragments cleaved from free dsRNA which direct the degradative mechanism to other similar RNA sequences. Both RNAi and translational repression are mediated by RISC. Both RNAi and translational repression occur naturally or can be initiated by the hand of man, for example, to silence the expression of target genes.

As used herein, the term "translational repression" refers to a selective inhibition of mRNA translation. Natural translational repression proceeds via miRNAs cleaved from shRNA precursors. Both RNAi and translational repression are mediated by RISC. Both RNAi and translational repression occur naturally or can be initiated by the hand of man, for example, to silence the expression of target genes.

As used herein, the term "small interfering RNA" ("siRNA") (also referred to in the art as "short interfering RNAs") refers to an RNA (or RNA analog) comprising between about 5-60 nucleotides (or nucleotide analogs) which is capable of directing or mediating RNA silencing (e.g., RNA interference or translational repression). Preferably, a siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising 5-23 nucleotides, preferably ~21 nucleotides (or nucleotide analogs), for example, 19, 20, 21 or 22 nucleotides. The term "long" siRNA refers to a siRNA comprising 24-60 nucleotides, preferably ~24-25 nucleotides, for example, 23, 24, 25 or 26 nucleotides. Short siRNAs may, in some instances, include fewer than 19 nucleotides, e.g., 16, 17 or 18 nucleotides, or as few as 5 nucleotides, provided that the shorter siRNA retains the ability to mediate RNAi. Likewise, long siRNAs may, in some instances, include more than 26 nucleotides, e.g., 27, 28, 29, 30, 35, 40, 45, 50, 55, or even 60 nucleotides, provided that the longer siRNA retains the ability to mediate RNAi or translational repression absent further processing, e.g., enzymatic processing, to a short siRNA.

As used herein, the term "microRNA" ("miRNA"), also referred to in the art as "small temporal RNAs" ("stRNAs"), refers to a small (10-50 nucleotide) RNA which are genetically encoded (e.g. by viral, mammalian, or plant genomes) and are capable of directing or mediating RNA silencing. An "miRNA disorder" shall refer to a disease or disorder characterized by an aberrant expression or activity of an miRNA.

As used herein, the term "antisense strand" of an RNA silencing agent, e.g. an siRNA or RNAi agent, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process (RNAi interference) or complementarity sufficient to trigger translational repression of the desired target mRNA.

The term "sense strand" or "second strand" of an RNA silencing agent, e.g. an siRNA or RNAi agent, refers to a strand that is complementary to the antisense strand or first strand. Antisense and sense strands can also be referred to as first or second strands, the first or second strand having complementarity to the target sequence and the respective second or first strand having complementarity to said first or second strand. miRNA duplex intermediates or siRNA-like duplexes include a miRNA strand having sufficient complementarity to a section of about 10-50 nucleotides of the mRNA of the gene targeted for silencing and a miRNA* strand having sufficient complementarity to form a duplex with the miRNA strand.

As used herein, the term "guide strand" refers to a strand of an RNAi agent, e.g., an antisense strand of an siRNA duplex or siRNA sequence, that enters into the RISC complex and directs cleavage of the target mRNA.

The term "engineered," as in an engineered RNA precursor, or an engineered nucleic acid molecule, indicates that the precursor or molecule is not found in nature, in that all or a portion of the nucleic acid sequence of the precursor or molecule is created or selected by man. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

An "isolated nucleic acid molecule or sequence" is a nucleic acid molecule or sequence that is not immediately contiguous with both of the coding sequences with which it is immediately contiguous (one on the 5' end and one on the 3' end) in the naturally occurring genome of the organism from which it is derived. The term therefore includes, for example, a recombinant DNA or RNA that is incorporated into a vector; into an autonomously replicating plasmid or virus; or into the genomic DNA of a prokaryote or eukaryote; or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide sequence.

As used herein, the term "isolated RNA" (e.g., "isolated shRNA", "isolated siRNA", "isolated siRNA-like duplex", "isolated miRNA", "isolated gene silencing agent", or "isolated RNAi agent") refers to RNA molecules which are substantially free of other cellular material, or culture medium when produced by recombinant techniques, or substantially free of chemical precursors or other chemicals when chemically synthesized.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and may include an enhancer sequence.

A gene "involved" in a disease or disorder includes a gene, the normal or aberrant expression or function of which effects or causes the disease or disorder or at least one symptom of said disease or disorder.

"Allele specific inhibition of expression" refers to the ability to significantly inhibit expression of one allele of a gene over another, e.g., when both alleles are present in the same cell. For example, the alleles can differ by one, two, three or more nucleotides. In some cases, one allele is associated with disease causation, e.g., a disease correlated to a dominant gain-of-function mutation.

The term "polyglutamine disorder" as used herein, refers to any disease or disorder characterized by an expanded of a $(CAG)_n$ repeats at the 5' end of the coding region (thus encoding an expanded polyglutamine region in the encoded protein). In one embodiment, polyglutamine disorders are characterized by a progressive degeneration of nerve cells. Examples of polyglutamine disorders include but are not limited to: Huntington's disease, spino-cerebellar ataxia type 1, spino-cerebellar ataxia type 2, spino-cerebellar ataxia type 3 (also know as Machado-Joseph disease), and spino-cerebellar ataxia type 6, spino-cerebellar ataxia type 7 and dentatoiubral-pallidoluysian atrophy.

The phrase "examining the function of a gene in a cell or organism" refers to examining or studying the expression, activity, function or phenotype arising therefrom.

Various methodologies of the instant invention include step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNAi agent of the invention into a cell or organism.

In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

"Treatment", or "treating" as used herein, is defined as the application or administration of a therapeutic agent (e.g., a RNA silencing agent or a vector or transgene encoding same) to a patient, or application or administration of a therapeutic agent to an isolated tissue or cell line from a patient, who has a disorder with the purpose to cure, heal, alleviate, delay, relieve, alter, remedy, ameliorate, improve or affect the disease or disorder, or symptoms of the disease or disorder. The term "treatment" or "treating" is also used herein in the context of administering agents prophylactically. The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. The term "patient" includes human and other mammalian subjects that receive either prophylactic or therapeutic treatment.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Various aspects of the invention are described in further detail in the following subsections.

Nucleic Acid Molecules

In one embodiment nucleic acid molecules are delivered to a target cell via a nanotransporter. As used herein the term "nucleic acid molecule" refers to a polymer of nucleotides joined together by a phosphodiester linkage between 5' and 3' carbon atoms. Nucleic acid molecules are generally known in the art, and include, but are not limited to siRNAs, chemically modified siRNAs, RNAi agents, miRNAs, shRNAs, antisense molecules, ribozymes, and the like.

a) Design of siRNA Molecules

An siRNA molecule of the invention is a duplex consisting of a sense strand and complementary antisense strand, the antisense strand having sufficient complementary to a target mRNA sequence to direct target-specific RNA interference (RNAi), as defined herein, i.e., the siRNA has a sequence sufficient to trigger the destruction of the target mRNA by the RNAi machinery or process.

Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is sufficiently complementary to a target region. Preferably, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is substantially complementary to a target region e.g., a gain-of-function gene target region, and the other strand is identical or substantially identical to the first strand.

Generally, siRNAs can be designed by using any method known in the art, for instance, by using the following protocol:

1. A target mRNA is selected and one or more target sites are identified within said target mRNA. Cleavage of mRNA at these sites results in mRNA degradation, preventing production of the corresponding protein. Polymorphisms from other regions of the mutant gene are also suitable for targeting.

In preferred embodiments, the target sequence comprises AA dinucleotide sequences; each AA and the 3' adjacent 16 or more nucleotides are potential siRNA targets. In another preferred embodiment, the nucleic acid molecules are selected from a region of the target mRNA sequence beginning at least 50 to 100 nt downstream of the start codon, e.g., of the sequence of the target mRNA. Further, siRNAs with lower G/C content (35-55%) may be more active than those with G/C content higher than 55%. Thus in one embodiment, the invention includes target sequences having 35-55% G/C content, although the invention is not limited in this respect.

2. The sense strand of the siRNA is designed based on the sequence of the selected target site. Preferably the sense strand includes about 19 to 25 nucleotides, e.g., 19, 20, 21, 22, 23, 24 or 25 nucleotides. More preferably, the sense strand includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention provided that they retain the ability to mediate RNAi. Longer RNAi agents have been demonstrated to elicit an interferon or PKR response in certain mammalian cells which may be undesirable. Preferably the RNAi agents of the invention do not elicit a PKR response (i.e., are of a sufficiently short length). However, longer RNAi agents may be useful, for example, in cell types incapable of generating a PRK response or in situations where the PKR response has been downregulated or dampened by alternative means.

The siRNA molecules of the invention have sufficient complementarity with the target site such that the siRNA can mediate RNAi. In general, siRNA containing nucleotide sequences sufficiently identical to a portion of the target gene to effect RISC-mediated cleavage of the target gene are preferred. Accordingly, in a preferred embodiment, the sense strand of the siRNA is designed have to have a sequence sufficiently identical to a portion of the target. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is preferred. The invention has the advantage of being able to tolerate certain sequence variations to enhance efficiency and specificity of RNAi. In one embodiment, the sense strand has 4, 3, 2, 1, or 0 mismatched nucleotide(s) with a target region, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al (1990) *J. Mol. Biol.* 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) *Nucleic Acids Res.* 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, *CABIOS* (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The anti sense strand sequence is designed such that nucleotides corresponding to the desired target cleavage site are essentially in the middle of the strand. For example, if a 21-nucleotide siRNA is chosen, nucleotides corresponding to the target cleavage site are at, for example, nucleotide 6, 7, 8, 9, 10, 11, 12, 13, 14, 15 or 16 (i.e., 6, 7, 8, 9, 10, 11, 12, 13, 14, 15 or 16 nucleotides from the 5' end of the sense strand. For a 22-nucleotide siRNA, nucleotides corresponding to the target cleavage site are at, for example, nucleotide 7, 8, 9, 10, 11, 12, 13, 14, 15 or 16. For a 23-nucleotide siRNA, nucleotides corresponding to the target cleavage site are at, for example, 7, 8, 9, 10, 11, 12, 13, 14, 15 or 16. For a 24-nucleotide siRNA, nucleotides corresponding to the target cleavage site are at, for example, 9, 10, 11, 12, 13, 14 or 16. For a 25-nucleotide siRNA, nucleotides corresponding to the target cleavage site are at, for example, 9, 10, 11, 12, 13, 14, 15, 16 or 17. Moving nucleotides corresponding to an off-center position may, in some instances, reduce efficiency of cleavage by the siRNA. Such compositions, i.e., less efficient compositions, may be desirable for use if off-silencing of a second (non-target) mRNA is detected.

The sense strand is designed such that complementarity exists between the antisense strand of the siRNA and the sense strand. In exemplary embodiments, the siRNA is designed such that the strands have overhanging ends, e.g., overhangs of 1, 2, 3, 4, 5 or more nucleotide at one, or both, ends of the siRNA. Exemplary overhangs are deoxynucleotide overhangs, for example, a dTdT tail.

4. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 4, e.g., 2, nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus in another embodiment, the nucleic acid molecules may have a 3' overhang of 2 nucleotides, such as TT. The overhanging nucleotides may be either RNA or DNA.

5. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

6. Select one or more sequences that meet your criteria for evaluation.

Further general information about the design and use of siRNA may be found in "The siRNA User Guide," available at The Max-Plank-Institut für Biophysikalishe Chemie website.

Alternatively, the siRNA may be defined functionally as comprising an antisense or guide strand having a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6 (log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA; a homology search can be performed to ensure that the negative control lacks homology to any other gene in the appropriate genome. In addition, negative control siRNAs can be designed by introducing a significant number of base mismatches into the sequence.

7. To validate the effectiveness by which siRNAs destroy mutant mRNAs (e.g., mutant huntingtin mRNA), the siRNA may be incubated with mutant cDNA (e.g., mutant huntingtin cDNA) in a *Drosophila*-based in vitro mRNA expression system. Radiolabeled with $^{32}P$, newly synthesized mutant mRNAs (e.g., mutant huntingtin mRNA) are detected autoradiographically on an agarose gel. The presence of cleaved mutant mRNA indicates mRNA nuclease activity. Suitable controls include omission of siRNA. Alternatively, control siRNAs are as described above are utilized.

b) miRNAs miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof.

The miRNA sequence can be similar or identical to that of any naturally occurring miRNA (see e.g. The miRNA Registry; Griffiths-Jones S, Nuc. Acids Res., 2004). Over one thousand natural miRNAs have been identified to date and together they are thought to comprise ~1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. MiRScan, MiR-Seeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (The miRNA Registry at the Sanger Institute website; Griffiths-Jones S, Nuc. Acids Res., 2004). Exemplary, natural miRNAs include lin-4, let-7, miR-10, mirR-15, miR-16, miR-168, miR-175, miR-196 and their homologs, as well as other natural miRNAs from humans and certain model organisms including *Drosophila melanogaster, Caenorhabditis elegans*, zebrafish, *Arabidopsis thalania*, mouse, and rat as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNAses (Lagos-Quintana et al., Science, 2001; Lau et al., Science, 2001; Lee and Ambros, Science, 2001; Lagos-Quintana et al., Curr. Biol., 2002; Mourelatos et al., Genes Dev., 2002; Reinhart et al., Science, 2002; Ambros et al., Curr. Biol., 2003; Brennecke et al., 2003; Lagos-Quintana et al., RNA, 2003; Lim et al., Genes Dev., 2003; Lim et al., Science, 2003). miRNAs can exist transiently in vivo as a double-stranded duplex but only one strand is taken up by the RISC complex to direct gene silencing. Certain miRNAs, e.g. plant miRNAs, have perfect or near-perfect complementarity to their target mRNAs and, hence, direct cleavage of the target mRNAs. Other miRNAs have less than perfect complementarity to their target mRNAs and, hence, direct translational repression of the target mRNAs. The degree of complementarity between an miRNA and its target mRNA is believed to determine its mechanism of action. For example, perfect or near-perfect complementarity between a miRNA and its target mRNA is predictive of a cleavage mechanism (Yekta et al., *Science,* 2004), whereas less than perfect complementarity is predictive of a translational repression mechanism. In particular embodiments, the miRNA sequence is that of a naturally-occurring miRNA sequence, the aberrant expression or activity of which is correlated with a miRNA disorder.

Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the invention are artificial constructs based on these naturally occurring pre-miRNAs, but which are engineered to deliver desired RNAi agents (e.g., siRNAs of the invention). By substituting the stem sequences of the pre-miRNA with sequence complementary to the target mRNA, a shRNA is formed. The shRNA is processed by the entire gene silencing pathway of the cell, thereby efficiently mediating RNAi.

In embodiments, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

c) siRNA-Like Molecules siRNA-like molecules of the invention have a sequence (i.e., have a strand having a sequence) that is "sufficiently complementary" to a target mRNA sequence to direct gene silencing either by RNAi or translational repression. siRNA-like molecules are designed in the same way as siRNA molecules, but the degree of sequence identity between the sense strand and target RNA approximates that observed between an miRNA and its target. In general, as the degree of sequence identity between a miRNA sequence and the corresponding target gene sequence is decreased, the tendency to mediate post-transcriptional gene silencing by translational repression rather than RNAi is increased.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the guide strand and the target mRNA contains a central "bulge" (Doench J G et al., Genes & Dev., 2003). In another embodiment 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further preferred embodiment, the "bulge" is centered at nucleotide positions 12 and 13 from the 5' end of the siRNA-like molecule.

d) Dual Functional Oligonucleotide Tethers

In other embodiments, the RNA silencing agents of the present invention include dual functional oligonucleotide tethers useful for the intercellular recruitment of a miRNA. Animal cells express a range of miRNAs, noncoding RNAs of approximately 22 nucleotides which can regulate gene expression at the post transcriptional or translational level. By binding a miRNA bound to RISC and recruiting it to a target mRNA, a dual functional oligonucleotide tether can repress the expression of genes involved e.g., in the arteriosclerotic process. The use of oligonucleotide tethers offer several advantages over existing techniques to repress the expression of a particular gene. First, the methods described herein allow an endogenous molecule (often present in abundance), an miRNA, to mediate RNA silencing; accordingly the methods described herein obviate the need to introduce foreign molecules (e.g., siRNAs) to mediate RNA silencing. Second, the RNA-silencing agents and, in particular, the linking moiety (e.g., oligonucleotides such as the 2'-O-methyl oligonucleotide), can be made stable and resistant to nuclease activity. As a result, the tethers of the present invention can be designed for direct delivery, obviating the need for indirect delivery (e.g. viral) of a precursor molecule or plasmid designed to make the desired agent within the cell. Third, tethers and their respective moieties, can be designed to conform to specific mRNA sites and specific miRNAs. The designs can be cell and gene product specific. Fourth, the methods disclosed herein leave the mRNA intact, allowing one skilled in the art to block protein synthesis in short pulses using the cell's own machinery. As a result, these methods of RNA silencing are highly regulatable.

The dual functional oligonucleotide tethers ("tethers") of the invention are designed such that they recruit miRNAs (e.g., endogenous cellular miRNAs) to a target mRNA so as to induce the modulation of a gene of interest. In preferred embodiments, the tethers have the formula T-L-$\mu$, wherein T is an mRNA targeting moiety, L is a linking moiety, and $\mu$ is an miRNA recruiting moiety. Any one or more moiety may be double stranded. Preferably, however, each moiety is single stranded.

Moieties within the tethers can be arranged or linked (in the 5' to 3' direction) as depicted in the formula T-L-$\mu$ (i.e., the 3' end of the targeting moiety linked to the 5' end of the linking moiety and the 3' end of the linking moiety linked to the 5' end of the miRNA recruiting moiety). Alternatively, the moieties can be arranged or linked in the tether as follows: $\mu$-T-L (i.e., the 3' end of the miRNA recruiting moiety linked to the 5' end of the linking moiety and the 3' end of the linking moiety linked to the 5' end of the targeting moiety).

The mRNA targeting moiety, as described above, is capable of capturing a specific target mRNA. According to the invention, expression of the target mRNA is undesirable, and, thus, translational repression of the mRNA is desired. The mRNA targeting moiety should be of sufficient size to effectively bind the target mRNA. The length of the targeting moiety will vary greatly depending, in part, on the length of the target mRNA and the degree of complementarity between the target mRNA and the targeting moiety. In various embodiments, the targeting moiety is less than about 200, 100, 50, 30, 25, 20, 19, 18, 17, 16, 15, 14, 13, 12, 11, 10, 9, 8, 7, 6, or 5 nucleotides in length. In a particular embodiment, the targeting moiety is about 15 to about 25 nucleotides in length.

The miRNA recruiting moiety, as described above, is capable of associating with an miRNA. According to the invention, the miRNA may be any miRNA capable of repressing the target mRNA. Mammals are reported to have over 250 endogenous miRNAs (Lagos-Quintana et al. (2002) Current Biol. 12:735-739; Lagos-Quintana et al. (2001) Science 294: 858-862; and Lim et al. (2003) Science 299:1540). In various embodiments, the miRNA may be any art-recognized miRNA.

The linking moiety is any agent capable of linking the targeting moieties such that the activity of the targeting moieties is maintained. Linking moieties are preferably oligonucleotide moieties comprising a sufficient number of nucleotides such that the targeting agents can sufficiently interact with their respective targets. Linking moieties have little or no sequence homology with cellular mRNA or miRNA sequences. Exemplary linking moieties include one or more 2'-O-methylnucleotides, e.g., 2'-O-methyladenosine, 2'-O-methylthymidine, 2'-O-methylguanosine or 2'-O-methyluridine.

e) Discriminatory RNA Silencing Agents

In other aspects, any of the RNA silencing agents described supra may be designed such that they are capable of discriminatory RNA silencing. For example, RNA silencing agents (e.g., siRNAs) which discriminate between RNAs of related sequences may be designed. Such agents are capable of silencing a target mRNA (e.g., an mRNA associated with a disease-associated allelic polymorphism) while failing to substantially silence a related non-target mRNA (e.g., an mRNA associated with a wild-type allele corresponding to the disease allele). In certain embodiments, RNA silencing agents capable of discriminatory RNA silencing may be designed by including a nucleotide which forms a Watson-Crick base pair with an allelic polymorphism in the target mRNA (e.g., a single-nucleotide polymorphism (SNP)) but which does not form a Watson-Crick base pair but a mismatched or wobble base pair with the corresponding nucleotide in the target mRNA (e.g., wild type). For example, the RNA silencing agent may be designed such that a mismatch (e.g., a purine:purine mismatch) or wobble exists between the siRNA and the non-target mRNA (e.g., wild type mRNA) at the single nucleotide. The purine:purine paring is selected, for example, from the group G:G, A:G, G:A and A:A pairing. Moreover, purine:pyrimidine pairing between the siRNA and the target mRNA (e.g mutant mRNA) at the single nucleotide enhances single nucleotide specificity. The purine:pyrimidine paring is selected, for example, from the group G:C, C:G, A:U, U:A, C:A, A:C, U:A and A:U pairing.

In other embodiments, the RNA silencing agents may be designed to discriminate between the non-target mRNA and the target mRNA by the introduction of a modified base positioned opposite the allelic polymorphism, such that the siRNA directs allele-specific cleavage of a mRNA comprising said polymorphism. Said methods are described in International PCT Publication No. WO 04/046324, which is incorporated herein by reference. In preferred embodiments, the modified base is selected from the group consisting of 5-bromo-uridine, 5-bromo-cytidine, 5-iodo-uridine, 5-iodo-cytidine, 2-amino-purine, 2-amino-allyl-purine, 6-amino-purine, 6-amino-allyl-purine, 2,6-diaminopurine and 6-amino-8-bromo-purine. In an exemplary embodiment, the modified base is 5-bromo-uridine or 5-iodo-uridine and, e.g., the point mutation is an adenine. In another exemplary embodiment, the modified base is 2,6-diaminopurine and, e.g., the point mutation is a thymine.

f) Chemically Modified Small Interfering RNA (siRNA) Molecules

In one aspect, the invention features RNAi agents, e.g., small interfering RNAs (siRNAs) that include a sense strand and an antisense strand, wherein the antisense strand has a sequence sufficiently complementary to a target mRNA sequence to direct target-specific RNA interference (RNAi) and wherein the sense strand and/or antisense strand is modified by the substitution of one or more nucleotides with chemically modified nucleotides. In one embodiment, the sense strand and/or the antisense strand are modified with one or more internal chemical modifications. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or the antisense strand are modified at the 5' end and/or the 3' end. In one embodiment, the sense strand and/or the antisense strand are modified at both the 5'end and the 3' end. As used herein, the term "modified at the end" or "end-modified" when used in reference to the 5' or 3' ends, refers to any nucleotide within 10 nucleotides of the first and last nucleotide, for example any nucleotide within 7 nucleotides of the first and last nucleotide. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the nucleotides. In yet another embodiment, the sense strand and/or antisense strand is modified by the substitution of all of the nucleotides. Within the RNAi agents employed in the methods of the invention, as few as one and as many as all nucleotides of the oligonucleotide can be modified. In some embodiments, the RNAi agent will contain as few modified nucleotides as are necessary to achieve a desired level of in vivo stability and/or bioaccessibility while maintaining cost effectiveness.

Chemical modifications may lead to increased stability, e.g., increased in vivo stability, compared to an unmodified RNAi agent or a label that can be used, e.g., to trace the RNAi agent, to purify an RNAi agent, or to purify the RNAi agent and cellular components with which it is associated. Such chemical modifications can also be used to stabilize the first (priming) strand of the siRNA for enhancing RISC activity/RNAi responsiveness in a cell (or cell extract or organism) and improve its intracellular half-life for subsequent receipt of the second strand wherein RNAi/gene silencing can now progress. Modifications can also enhance properties such as cellular uptake of the RNAi agents and/or stability of the RNAi agents, can stabilize interactions between base pairs, and can maintain the structural integrity of the antisense RNAi agent-target RNA duplex. RNAi agent modifications can also be designed such that properties important for in vivo applications, in particular, human therapeutic applications, are improved without compromising the RNAi activity of the RNAi agents e.g., modifications to increase resistance of, e.g., siRNA or miRNA molecules to nucleases. In certain embodiments, modified siRNA molecules of the invention can enhance the efficiency of target RNA inhibition as compared to a corresponding unmodified siRNA. In some embodiments, modified nucleotides do not affect the ability of the antisense strand to adopt A-form helix conformation when base-pairing with the target RNA sequence, e.g., an A-form helix conformation comprising a normal major groove when base-pairing with the target RNA sequence.

Chemical modifications generally include end-, sugar-, base- and/or backbone-modifications to the ribonucleotides (i.e., include modifications to the phosphate-sugar backbone).

In one embodiment, the RNAi agent of the invention comprises one or more (e.g., about 1, 2, 3, or 4) end modifications. For example, modification at the 5' end of an siRNA molecule comprises, for example, a 5'-propylamine group or a fluourescent molecule, e.g., Cy3. Modifications of the 5' end may also include 5' terminal phosphate groups, such as those described by Figure I:

(I)

wherein each X and Y is independently O, S, N, alkyl, substituted alkyl, or alkylhalo; wherein each Z and W is independently O, S, N, alkyl, substituted alkyl, O-alkyl, S-alkyl, alkaryl, aralkyl, alkylhalo, or acetyl. In some embodiments, W, X, Y and Z are not all O. Modifications to the 3' OH terminus of an siRNA molecule can include, but are not limited to, 3'-puromycin, 3'-biotin (e.g., a photocleavable biotin), a peptide (e.g., a Tat peptide), a nanoparticle, a peptidomimetic, organic compounds (e.g., a dye such as a fluorescent dye), or a dendrimer. End modifications may be on the sense strand, on the antisense strand or both. In some embodiments, the 5' modifications are on the sense strand only.

In another embodiment, the RNAi agent of the invention may comprise one or more (e.g., about 1, 2, 3, 4, 5, 6, 7, 8, 9, 10, or more) sugar-modified nucleotides. Exemplary sugar modifications may include modifications represented by Formula II:

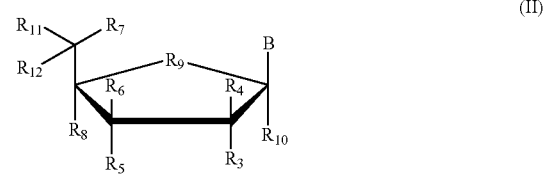

(II)

wherein each $R_3$, $R_4$, $R_5$, $R_6$, $R_7$, $R_8$, $R_{10}$, $R_{11}$ and $R_{12}$ is independently H, OH, alkyl, substituted alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-S-alkyl, alkyl-O-alkyl, $ONO_2$, $NO_2$, $N_3$, $NH_2$, aminoalkyl, aminoacid, aminoacyl, $ONH_2$, O-aminoalkyl, O-aminoacid, or O-aminoacyl, heterocycloalkyl, heterocycloalkaryl, aminoalkylamino, polyalkylamino, substituted silyl; $R_9$ is O, S, $CH_2$, S=O, CHF, or $CF_2$, and B is a nucleosidic base. Sugar-modified nucleotides include, but are not limited to: 2'-fluoro modified ribonucleotides, 2'-OMe modified ribonucleotides, 2'-deoxy ribonucleotides, 2'-amino modified ribonucleotides and 2'-thio modified ribonucleotides. The sugar-modified nucleotide can be, for example, 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine or 2'-amino-butyryl-pyrene-uridine. In one embodiment, the sugar-modified nucleotide is a 2'-fluoro ribonucleotide. In some embodiments, when a 2'-deoxy ribonucleotide is present, it is upstream of the cleavage site referencing the antisense strand or downstream of the cleavage site referencing the antisense strand. The 2'-fluoro ribonucleotides can be in the sense and antisense strands. In some embodiments, the 2'-fluoro ribonucleotides are every uridine and cytidine. In other embodiments, the 2'-fluoro ribonucleotides are only present at the 3' and 5' ends of the sense strand, the antisense strand or both.

In another embodiment, the RNAi agent of the invention comprises one or more (e.g., about 1, 2, 3, 4, 5, 6, 7, 8, 9, 10, or more) nucleobase-modified nucleotides. Nucleobase-modified nucleotides useful in the invention include, but are not limited to: uridine and/or cytidine modified at the 5-position (e.g., 5-bromo-uridine, 5-(2-amino)propyl uridine, 5-amino-allyl-uridine, 5-iodo-uridine, 5-methyl-cytidine, 5-fluoro-cytidine, and 5-fluoro-uridine), ribo-thymidine, 2-aminopurine, 2,6-diaminopurine, 4-thio-uridine, adenosine and/or guanosines modified at the 8 position (e.g., 8-bromo guanosine), deaza nucleotides (e.g., 7-deaza-adenosine), O- and N-alkylated nucleotides (e.g., N6-methyl adenosine) and non-nucleotide-type bases (e.g., deoxy-abasic, inosine, N3-methyl-uridine, N6,N6-dimethyl-adenosine, pseudouridine, purine ribonucleoside and ribavirin).

In another embodiment, the RNAi agent of the invention comprises one or more (e.g., about 1, 2, 3, 4, 5, 6, 7, 8, 9, 10, or more) backbone-modified nucleotides. For example, backbone modifications may include modifications represented by Formula III:

(III)

wherein each $R_1$ and $R_2$ is independently any nucleotide as described herein, each X and Y is independently O, S, N, alkyl, or substituted alkyl, each Z and W is independently O, S, N, alkyl, substituted alkyl, O-alkyl, S-alkyl, alkaryl, aralkyl, or acetyl. In some embodiments, W, X, Y, and Z are not all O. Exemplary backbone-modified nucleotides contain a phosphorothioate group or a phosphorodithioate. In another embodiment, a backbone modification of the invention comprises a phosphonoacetate and/or thiophosphonoacetate internucleotide linkage (see for example Sheehan et al., 2003, Nucleic Acids Research, 31, 4109-4118). The backbone-modifications can be within the sense strand, antisense strand, or both the sense and antisense strands. In some embodiments, only a portion of the internucleotide linkages are modified in one or both strands. In other embodiments, all of the internucleotide linkages are modified in one or both strands. In one embodiment, the modified internucleotide linkages are at the 3' and 5' ends of one or both strands.

In another embodiment, an siRNA molecule of the invention may comprise one or more (e.g., about 1, 2, 3, 4, 5, 6, 7, 8, 9, 10, or more) crosslinks, e.g., a crosslink wherein the sense strand is crosslinked to the antisense strand of the siRNA duplex. Crosslinkers useful in the invention are those commonly known in the art, e.g., psoralen, mitomycin C, cisplatin, chloroethylnitrosoureas and the like. In one embodiment, the crosslink of the invention is a psoralen crosslink. Preferably, the crosslink is present downstream of the cleavage site referencing the antisense strand, and more preferably, the crosslink is present at the 5' end of the sense strand.

In another embodiment, the RNAi agent of the invention comprises a sequence wherein the antisense strand and target mRNA sequences comprise one or more (e.g., about 1, 2, 3, 4, 5, 6, 7, 8, 9, 10, or more) mismatches. In some embodiments, the mismatch is downstream of the cleavage site referencing the antisense strand, e.g., within 1-6 nucleotides from the 3' end of the antisense strand. In another embodiment, the RNAi agent of the invention is an siRNA molecule that comprises a bulge, e.g., one or more (e.g., about 1, 2, 3, 4, 5, 6, 7, 8, 9, 10, or more) unpaired bases in the duplex siRNA. In some embodiments, the bulge is in the sense strand.

It is to be understood that any of the above combinations can be used in any combination to provide the modified RNAi agents of the present invention. For example, in some embodiments, the invention includes an siRNA, wherein the sense strand includes one or more (e.g., about 1, 2, 3, 4, 5, 6, 7, 8, 9, 10, or more) phosphorothioate internucleotide linkages, and/or one or more (e.g., about 1, 2, 3, 4, 5, 6, 7, 8, 9, 10 or more) 2'-deoxy, 2'-O-methyl, and/or 2'-fluoro sugar modifications, and/or one or more (e.g., about 1, 2, 3, 4, 5, 6, 7, 8, 9, 10 or more) base modified nucleotides, and/or an end-modification at the 3'-end, the 5'-end, or both the 3'- and 5'-ends of the sense strand. In some embodiments, the invention includes an siRNA, wherein the antisense strand includes one or more (e.g., about 1, 2, 3, 4, 5, 6, 7, 8, 9, 10, or more) phosphorothioate internucleotide linkages, and/or one or more (e.g., about 1, 2, 3, 4, 5, 6, 7, 8, 9, 10 or more) 2'-deoxy, 2'-O-methyl, and/or 2'-fluoro sugar modifications, and/or one or more (e.g., about 1, 2, 3, 4, 5, 6, 7, 8, 9, 10 or more) base modified nucleotides, and/or an end-modification at the 3'-end, the 5'-end, or both the 3'- and 5'-ends of the antisense strand. In yet other embodiments, the invention includes an siRNA, wherein both the sense strand and the antisense strand include one or more (e.g., about 1, 2, 3, 4, 5, 6, 7, 8, 9, 10, or more) phosphorothioate internucleotide linkages, and/or one or more (e.g., about 1, 2, 3, 4, 5, 6, 7, 8, 9, 10 or more) 2'-deoxy, 2'-O-methyl, and/or 2'-fluoro sugar modifications, and/or one or more (e.g., about 1, 2, 3, 4, 5, 6, 7, 8, 9, 10 or more) base modified nucleotides, and/or an end-modification at the 3'-end, the 5'-end, or both the 3'- and 5'-ends of either or both the sense strand and/or the antisense strand.

Modified RNAi agents of the invention (i.e., duplex siRNA molecules) can be modified at the 5' end, 3' end, 5' and 3' end, and/or at internal residues, or any combination thereof. RNAi agent modifications can be, for example, end modifications, sugar modifications, nucleobase modifications, backbone modifications, and can contain mismatches, bulges, or crosslinks. Also included are 3' end, 5' end, or 3' and 5' and/or internal modifications, wherein the modifications are, for example, cross linkers, heterofunctional cross linkers, and the like. RNAi agents of the invention also may be modified with chemical moieties (e.g., cholesterol) that improve the in vivo pharmacological properties of the RNAi agents.

In certain aspects of the present invention, the chemically modified siRNAs of the present invention are terminally-modified siRNAs. That is, the siRNAs are modified at one or both of the 3' end and the 5' end of the sense and/or antisense strand. In certain embodiments, the chemically modified siRNAs are modified at both the 3' end and the 5' end of both the sense antisense strand. In some embodiments, the 3' end and/or the 5' end of the sense and/or antisense strands are end-modified such that 2 or 3 or 4 modified nucleotides are incorporated per end (e.g., within the 5-7 terminal nucleotides, e.g., within the duplex). In some embodiments, the 3' end and/or the 5' end of the sense and/or antisense strands are end-modified such that 2 or 3 or 4 2'-fluoro nucleotides, e.g., 2' fluorocytidine and/or 2'fluorouracil, are incorporated per end (e.g., within the 5-7 terminal nucleotides, e.g., within the duplex). In some embodiments, the 3' end and/or the 5' end of the sense and/or antisense strands are end-modified such that 2 or 3 or 4 internucleotide linkages are phosphorothioate linkages per end (e.g., between the 5-7 terminal nucleotides, e.g., within the duplex). In some embodiments, the modifications include any of the modifications described herein. In other embodiments, the modifications include phosphorothioate linkages. In still other embodiments, the modifications include 2'-sugar modifications. In still other embodiments, the modifications include 2'-fluoro nucleotide modifications. In yet other embodiments, the modifications include both phosphorothioate linkages and 2'-fluoro nucleotide modifications.

In some embodiments, the chemically modified siRNA of the present invention comprises two strands, each according to formula IV:

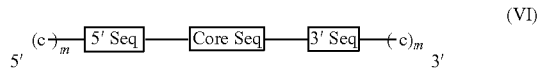

(VI)

wherein:

each occurrence of c is independently an end modification, e.g., a species according to formula I;

each occurrence of m is an integer of 0 or 1;

-5'Seq- and -3'Seq- each independently comprise 2-10 nucleotides, wherein the nucleotides are purine and pyrimidine nucleotides, wherein about 1-6 nucleotides are modified, e.g., a modification according to formula II, and wherein each internucleotide linkage in the unit is optionally modified, e.g., a modification according to formula III;

-CoreSeq- comprises 5-20 unmodified nucleotides linked via phosphate internucleotide linkages; and -5'Seq- is linked to -CoreSeq- via an optionally modified internucleotide linkage and -CoreSeq- is linked to -3'Seq- via an optionally modified internucleotide linkage.

In some embodiments, -5'Seq- is represented by the formula:

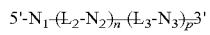

wherein:

n is an integer from 2-9;

p is an integer from 0-3;

$N_1$ is an unmodified nucleotide;

each occurrence of $N_2$ is independently selected from the group consisting of a modified purine nucleotide, an unmodified purine nucleotide and a modified pyrimidine nucleotide, wherein about 1-6 occurrences of $N_2$ are modified pyrimidine nucleotides;

each occurrence of $N_3$ is independently selected from the group consisting of a modified purine nucleotide, an unmodified purine nucleotide, a modified pyrimidine nucleotide and an unmodified pyrimidine nucleotide; and each occurrence of $L_2$ and $L_3$ are independently a phosphate linkage or a linkage according to formula III.

In some embodiments, about 2 occurrences of $N_2$ are modified pyrimidine nucleotides. In other embodiments, about 3 occurrences of $N_2$ are modified pyrimidine nucleotides. In other embodiments, about 4 occurrences of $N_2$ are modified pyrimidine nucleotides. In other embodiments, about 5 occurrences of $N_2$ are modified pyrimidine nucleotides.

In some embodiments, no occurrences of $L_2$ or $L_3$ are linkages according to formula III. In other embodiments, about 2-5 occurrences of $L_2$ and $L_3$ (taken together) are linkages according to formula III. For example, one occurrence of $L_2$ and one occurrence of $L_3$ (total 2 occurrences when $L_2$ and $L_3$ are taken together) may be linkages according to formula III. In some embodiments, no occurrences of $L_2$ are linkages according to formula III. In other embodiments, about 1 occurrence of $L_2$ is a linkage according to formula III. In other embodiments, about 2 occurrences of $L_2$ are linkages according to formula III. In other embodiments, about 4 occurrences of $L_2$ are linkages according to formula III. In other embodiments, about 5 occurrences of $L_2$ are linkages according to formula III. In some embodiments, no occurrences of $L_3$ are linkages according to formula III. In some embodiments, about 1 occurrences of $L_3$ are linkages according to formula III. In other embodiments, about 2 occurrences of $L_3$ are linkages according to formula III.

In some embodiments, the sense strand is a strand according to formula IV, wherein c is a Cy3 end modification or an end modification according to formula I and -5'Seq- is represented by the formula:

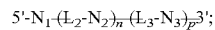

and wherein n is an integer from 4-9; p is 0; $N_1$ is an unmodified nucleotide; each occurrence of $N_2$ is independently selected from the group consisting of an unmodified purine nucleotide and a modified pyrimidine nucleotide, wherein about 1-6 occurrences of $N_2$ are modified pyrimidine nucleotides; and each occurrence of $L_2$ is independently a phosphate linkage or a linkage according to formula III. In some embodiments, about 2-4 occurrences of $N_2$ are modified pyrimidine nucleotides. In further embodiments, n is an integer of 5-7, each occurrence of $N_2$ is independently selected from the group consisting of an unmodified purine nucleotide and a 2'-fluoro-modified pyrimidine nucleotide, wherein about 1-6 occurrences of $N_2$ are 2'-fluoro-modified pyrimidine nucleotides; and about 1-4 occurrences of $L_2$ are linkages according to formula III. In still further embodiments, n is 6, about 2-4 occurrences of $N_2$ are 2'-fluoro-modified pyrimidine nucleotides; and about 2-3 occurrences of $L_2$ are linkages according to formula III.

In some embodiments, the antisense strand is a strand according to formula IV, wherein c is a 5' terminal phosphate modification and -5'Seq- is represented by the formula:

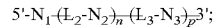

and wherein n is an integer from 3-7; p is 0-3; $N_1$ is an unmodified nucleotide; each occurrence of $N_2$ is independently selected from the group consisting of an unmodified purine nucleotide and a modified pyrimidine nucleotide, wherein about 1-6 occurrences of $N_2$ are modified pyrimidine nucleotides; each occurrence of $N_3$ is independently selected from the group consisting of an unmodified purine nucleotide and an unmodified pyrimidine nucleotide; and each occurrence of $L_2$ and $L_3$ are independently a phosphate linkage or a linkage according to formula III. In some embodiments, about 2-4 occurrences of $N_2$ are modified pyrimidine nucleotides. In some embodiments, each occurrence of $N_2$ is independently selected from the group consisting of an unmodified purine nucleotide and a 2'-fluoro-modified pyrimidine nucleotide, wherein about 1-6 occurrences of $N_2$ are 2'-fluoro-modified pyrimidine nucleotides; and each occurrence of $L_2$ is a phosphate linkage. In still further embodiments, n is 6; p is 0; and about 2-4 occurrences of $N_2$ are 2'-fluoro-modified pyrimidine nucleotides. In still further embodiments, n is 3; p is 3; and about 2-4 occurrences of $N_2$ are 2'-fluoro-modified pyrimidine nucleotides. In some embodiments, -5'Seq- is the seed sequence, and comprises nucleotides 2-7 of the siRNA.

In some embodiments, -CoreSeq- is represented by the formula:

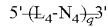

wherein:
q is an integer from 5-15;
each occurrence of $N_4$ is an unmodified nucleotide; and
each occurrence of $L_4$ is independently a phosphate linkage.

The skilled artisan would understand that -CoreSeq- could be modified, e.g., with one or more nucleotide modifications or internucleotide linkage modifications, without interfering with the activity of the siRNA. Accordingly, in some embodiments, -CoreSeq- may comprise certain modifications, e.g., 1, 2, 3, 4 or 5 nucleotide or internucleotide linkage modifications. In some embodiments, -CoreSeq- contains less than about 3, less than about 2, less than about 1 modification.

In some embodiments, -3' Seq- is represented by the formula:

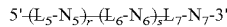

wherein:
r is an integer from 3-9;
s is an integer from 0 to 3;
$N_7$ is an unmodified nucleotide;
each occurrence of $N_5$ is independently selected from the group consisting of a modified purine nucleotide, an unmodified purine nucleotide and a modified pyrimidine nucleotide, wherein about 1-6 occurrences of $N_5$ are modified pyrimidine nucleotides;
each occurrence of $N_6$ is independently selected from the group consisting of a modified purine nucleotide, an unmodified purine nucleotide, a modified pyrimidine nucleotide and an unmodified pyrimidine nucleotide;
each occurrence of $L_5$ and $L_6$ are independently a phosphate linkage or a linkage according to formula III; and
$L_7$ is a linkage according to formula III.

In some embodiments, about 2 occurrences of $N_5$ are modified pyrimidine nucleotides. In other embodiments, about 3 occurrences of $N_5$ are modified pyrimidine nucleotides. In other embodiments, about 4 occurrences of $N_5$ are modified pyrimidine nucleotides. In other embodiments, about 5 occurrences of $N_5$ are modified pyrimidine nucleotides.

In some embodiments, about 2-5 occurrences of $L_5$ and $L_6$ (taken together) are linkages according to formula III. In other embodiments, about 1 occurrence of $L_5$ is a linkage according to formula III. In other embodiments, about 2 occurrences of $L_5$ are linkages according to formula III. In other embodiments, about 4 occurrences of $L_5$ are linkages according to formula III. In other embodiments, about 5 occurrences of $L_5$ are linkages according to formula III. In some embodiments, no occurrences of $L_6$ are linkages according to formula III. In some embodiments, about 1 occurrences of $L_6$ are linkages according to formula III. In other embodiments, about 2 occurrences of $L_6$ are linkages according to formula III.

In some embodiments, the sense strand is a strand according to formula IV, wherein -3'Seq- is represented by the formula:

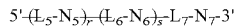

and wherein r is an integer from 4-9; s is 0; $N_7$ is an unmodified nucleotide; each occurrence of $N_5$ is independently selected from the group consisting of an unmodified purine nucleotide and a modified pyrimidine nucleotide, wherein about 1-6 occurrences of $N_5$ are modified pyrimidine nucleotides; and each occurrence of $L_5$ is independently a phosphate linkage or a linkage according to formula III. In some embodiments, about 2-4 occurrences of $N_5$ are modified pyrimidine nucleotides. In further embodiments, r is an integer of 5-7, each occurrence of $N_5$ is independently selected from the group consisting of an unmodified purine nucleotide and a 2'-fluoro-modified pyrimidine nucleotide, wherein about 1-6 occurrences of Ns are 2'-fluoro-modified pyrimidine nucleotides; and about 14 occurrences of $L_5$ is a linkage according to formula III. In still further embodiments, r is 6, about 2-4 occurrences of Ns are 2'-fluoro-modified pyrimidine nucleotides; and about 2-3 occurrences of $L_5$ are linkages according to formula III.

In some embodiments, the antisense strand is a strand according to formula IV, wherein -3'Seq- is represented by the formula:

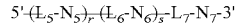

and wherein r is an integer from 3-7; s is 0-3; $N_7$ is an unmodified nucleotide; each occurrence of $N_5$ is independently selected from the group consisting of an unmodified purine nucleotide and a modified pyrimidine nucleotide, wherein about 1-6 occurrences of $N_5$ are modified pyrimidine nucleotides; each occurrence of $N_6$ is independently selected from the group consisting of an unmodified purine nucleotide and an unmodified pyrimidine nucleotide; and each occurrence of $L_5$ and $L_6$ are independently a phosphate linkage or a linkage according to formula III. In some embodiments, about 2-4 occurrences of $N_5$ are modified pyrimidine nucleotides. In some embodiments, each occurrence of $N_5$ is independently selected from the group consisting of an unmodified purine nucleotide and a 2'-fluoro-modified pyrimidine nucleotide, wherein about 1-6 occurrences of $N_5$ are 2'-fluoro-modified pyrimidine nucleotides; about 2-4 occurrences of $L_5$ are linkages according to formula III. In still further embodiments, r is 6; s is 0; and about 2-4 occurrences of $N_5$ are 2'-fluoro-modified pyrimidine nucleotides. In still further embodiments, r is 5; s is 1; and about 2-4 occurrences of $N_2$ are 2'-fluoro-modified pyrimidine nucleotides.

Accordingly, in some embodiments, the chemically modified siRNA of the present invention comprises two strands, each according to formula V:

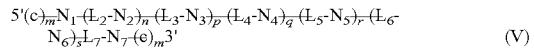  (V)

wherein c, m, n, p, q, r, s, $N_1$, $N_2$, $N_3$, $N_4$, $N_5$, $N_6$, $N_7$, $L_2$, $L_3$, $L_4$, $L_5$, $L_6$, and $L_7$ are all defined as above. It is to be understood that all integer values and ranges between the values and ranges listed herein, e.g., in relation to m, n, p, q, r and s, and/or in relation to the number of occurrences of modified and unmodified $N_2$, $N_3$, $N_4$, $N_5$, $N_6$, $L_2$, $L_3$, $L_4$, $L_5$ and $L_6$, and are meant to be encompassed by the present invention.

Specific modifications include, but are not limited to those shown in FIG. 1 as well as below in Table 1.

TABLE 1

Exemplary chemically modified siRNAs (target ApoB)

5'-P-A-2'FU-2'FU-G-GUAUUCAGUGUG-A-2'FU-G-A-2'FC*A*C-3'    Seq Id 1

TABLE 1-continued

Exemplary chemically modified siRNAs
(target ApoB)

| | |
|---|---|
| 5'-P-G*2'FU-2'FC-A-2'FU-2'FC-A-CACUGAAUA-2'FC-2'FC-A-A*2'FU-N3-3' | Seq Id 2 |
| 5'-P-G-2'FU-G-A-2'FU-2'FC-A-GACUCAAU-A-2'FC-G-A-A*2'FU-N3-3' | Seq Id 3 |
| 5'-P-A-2'FU-2'FU-C-GUAUUGAGUCU-G-A-2'FU-C-A-2'FC*A*C-3' | Seq Id 4 |

Modification key:
2'FU/FC = 2'fluorouricil/fluorocytidine
* = phosphorothioate backbone linkage
- = normal backbone linkage
N3 = propylamine In some embodiments, the RNAi agent of the instant invention may also contain a nuclear localization/nuclear targeting signal(s). Such modifications may be made exclusive of, or in addition to, any combination of other modifications as described herein. Nuclear targeting signals include any art-recognized signal capable of effecting a nuclear localization to a molecule, including, for example, NLS signal sequence peptides.

Moreover, because RNAi is believed to progress via at least one single stranded RNA intermediate, the skilled artisan will appreciate that ss-siRNAs (e.g., the antisense strand of a ds-siRNA) can also be designed as described herein and utilized according to the claimed methodologies.

Oligonucleotide RNAi agents may be produced enzymatically or by partial/total organic synthesis. In one embodiment, an RNAi agent, e.g., siRNA, is prepared chemically. Methods of synthesizing RNA and DNA molecules are known in the art, in particular, the chemical synthesis methods as described in Verma and Eckstein (1998) *Annul Rev. Biochem.* 67:99-134. RNA can be purified from a mixture by extraction with a solvent or resin, precipitation, electrophoresis, chromatography, or a combination thereof. Alternatively, the RNA may be used with no or a minimum of purification to avoid losses due to sample processing. Alternatively, the RNA molecules, e.g., RNAi oligonucleotides, can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) *Methods Enzymol.* 180:51-62). The RNA may be dried for storage or dissolved in an aqueous solution. The solution may contain buffers or salts to inhibit annealing, and/or promote stabilization of the single strands.

In one embodiment, siRNAs are synthesized either in vivo, in situ, or in vitro. Endogenous RNA polymerase of the cell may mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the siRNA. Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses siRNA from a recombinant construct may be produced by introducing the construct into a zygote, an embryonic stem cell, or another multipotent cell derived from the appropriate organism.

Expression levels of target and any other surveyed RNAs and proteins may be assessed by any of a wide variety of well known methods for detecting expression of non-transcribed nucleic acid, and transcribed nucleic acid or protein. Non-limiting examples of such methods include RT-PCR of RNA followed by size separation of PCR products, nucleic acid hybridization methods e.g., Northern blots and/or use of nucleic acid arrays; nucleic acid amplification methods; immunological methods for detection of proteins; protein purification methods; and protein function or activity assays. RNA expression levels can be assessed by preparing mRNA/cDNA (i.e. a transcribed polynucleotide) from a cell, tissue or organism, and by hybridizing the mRNA/cDNA with a reference polynucleotide which is a complement of the assayed nucleic acid, or a fragment thereof. cDNA can, optionally, be amplified using any of a variety of polymerase chain reaction or in vitro transcription methods prior to hybridization with the complementary polynucleotide; preferably, it is not amplified. Expression of one or more transcripts can also be detected using quantitative PCR to assess the level of expression of the transcript(s).

Knockout and/or Knockdown Cells or Organisms

A further preferred use for the siRNA molecules of the present invention (or vectors or transgenes encoding same) is a functional analysis to be carried out in eukaryotic cells, or eukaryotic non-human organisms, preferably mammalian cells or organisms and most preferably human cells, e.g. cell lines such as HeLa or 293 or rodents, e.g. rats and mice. By administering a suitable siRNA molecules which is sufficiently complementary to a target mRNA sequence to direct target-specific RNA interference, a specific knockout or knockdown phenotype can be obtained in a target cell, e.g. in cell culture or in a target organism.

Thus, a further subject matter of the invention is a eukaryotic cell or a eukaryotic non-human organism exhibiting a target gene-specific knockout or knockdown phenotype comprising a fully or at least partially deficient expression of at least one endogenous target gene wherein said cell or organism is transfected with at least one vector comprising DNA encoding a siRNA molecule capable of inhibiting the expression of the target gene. It should be noted that the present invention allows a target-specific knockout or knockdown of several different endogenous genes due to the specificity of the siRNAi.

Gene-specific knockout or knockdown phenotypes of cells or non-human organisms, particularly of human cells or non-human mammals may be used in analytic to procedures, e.g. in the functional and/or phenotypical analysis of complex physiological processes such as analysis of gene expression profiles and/or proteomes. Preferably the analysis is carried out by high throughput methods using oligonucleotide based chips.

mRNA Targets

In one embodiment, the target mRNA of the invention specifies the amino acid sequence of a cellular protein (e.g., a nuclear, cytoplasmic, transmembrane, or membrane-associated protein). In another embodiment, the target mRNA of the invention specifies the amino acid sequence of an extracellular protein (e.g., an extracellular matrix protein or secreted protein). As used herein, the phrase "specifies the amino acid sequence" of a protein means that the mRNA sequence is translated into the amino acid sequence according to the rules of the genetic code. The following classes of proteins are listed for illustrative purposes: developmental proteins (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogene-encoded proteins (e.g., ABLI, BCLI, BCL2, BCL6, CBFA2, CBL, CSFIR, ERBA, ERBB, EBRB2, ETSI, ETSI, ETV6, FGR, FOS, FYN, HCR, HRAS, JUN, KRAS, LCK, LYN, MDM2, MLL, MYB, MYC, MYCLI, MYCN, NRAS, PIM I, PML, RET, SRC, TALI, TCL3, and YES); tumor suppressor proteins (e.g., APC, BRCA1, BRCA2, MADH4, MCC, NF I, NF2, RB I, TP53, and WTI); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextriinases, DNA and RNA polymerases, galactosidases, glucanases, glucose oxidases, granule-bound starch synthases, GTPases, helicases, hernicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases).

In a preferred aspect of the invention, the target mRNA molecule of the invention specifies the amino acid sequence of a protein associated with a pathological condition. For example, the protein may be a pathogen-associated protein (e.g., a viral protein involved in immunosuppression of the host, replication of the pathogen, transmission of the pathogen, or maintenance of the infection), or a host protein which facilitates entry of the pathogen into the host, drug metabolism by the pathogen or host, replication or integration of the pathogen's genome, establishment or spread of infection in the host, or assembly of the next generation of pathogen. Alternatively, the protein may be a tumor-associated protein or an autoimmune disease-associated protein.

In one embodiment, the target mRNA molecule of the invention specifies the amino acid sequence of an endogenous protein (i.e., a protein present in the genome of a cell or organism). In another embodiment, the target mRNA molecule of the invention specified the amino acid sequence of a heterologous protein expressed in a recombinant cell or a genetically altered organism. In another embodiment, the target mRNA molecule of the invention specified the amino acid sequence of a protein encoded by a transgene (i.e., a gene construct inserted at an ectopic site in the genome of the cell). In yet another embodiment, the target mRNA molecule of the invention specifies the amino acid sequence of a protein encoded by a pathogen genome which is capable of infecting a cell or an organism from which the cell is derived.

By inhibiting the expression of such proteins, valuable information regarding the function of said proteins and therapeutic benefits which may be obtained from said inhibition may be obtained.

SOD-1 Gene

In one embodiment, the target mRNA is a SOD1 mRNA. SOD1 is a metalloenzyme that contains one copper and one zinc, and is present in the cytoplasm as a homodimer. Copper is required for enzymatic activity while zinc stabilizes the protein's structure (Fridovich, 1986). SOD1 is a expressed in all eukaryotic cells and is one of a family of three SOD enzymes, including manganese-dependent, mitochondrial SOD (SOD2) and copper/zinc extracellular SOD (SOD3) (I Fridovich, 1986, "Superoxide dismutases," Advances in Enzymology 58: 61-97). The main natural function of SOD1 is superoxide dismutation, in which superoxide ($O_2^-$) is converted to hydrogen peroxide ($H_2O_2$) and oxygen. Together with the downstream enzymes catalase and glutathione peroxidase (which convert $H_2O_2$ to water and oxygen), SOD1 detoxifies cellular free radicals. The importance of this function is underscored by numerous abnormalities in mice lacking the SOD1 gene, including reduced fertility (Matzuk et al., 1998), motor axonopathy (Shefner et al., 1999), increased age-associated loss of cochlear hair cells (McFadden et al., 2001) and neuromuscular junction synapses (Flood et al., 1999), and enhanced susceptibility to a variety of noxious assaults on the nervous system, such as axonal injury (Reaume et al., 1996), ischemia (Kondo et al., 1997; Kawase et al., 1999), hemolysate exposure (Matz et al., 2000) and irradiation (Behndig et al., 2001). Given the toxicity of the mutant protein and the functional importance of the wild-type, the ideal therapy for ALS would be to preferentially block expression of (e.g., knock down) the mutant SOD1 protein as compared to expression of the wild-type SOD1 protein.

Figure 3A:
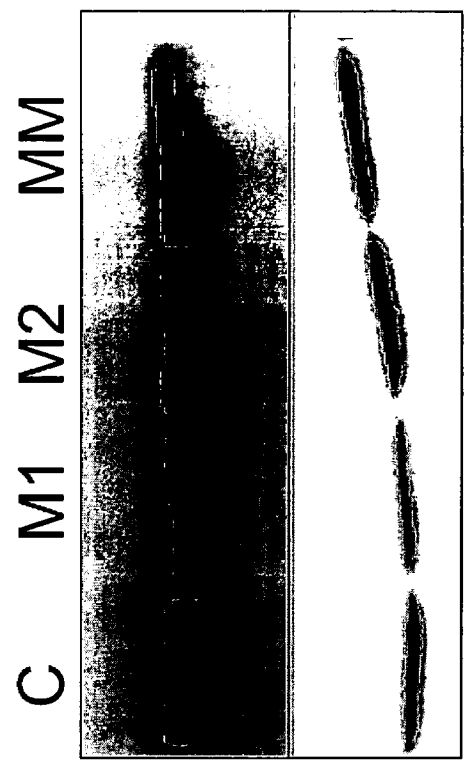
FIG. 3 depicts silencing effects of terminally-modified siRNAs against endogenous SOD1 in transfected HEK293 cells and in vivo (FIG. 3A).
FIG. 3B depicts quantitative silencing effect of R1 and R2 siRNAs.
Figure 3B:
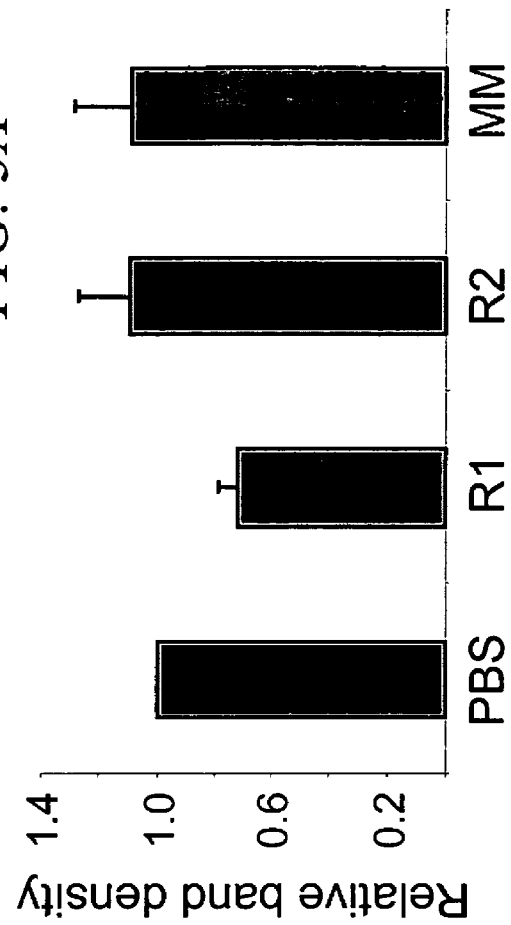
Figure 5:
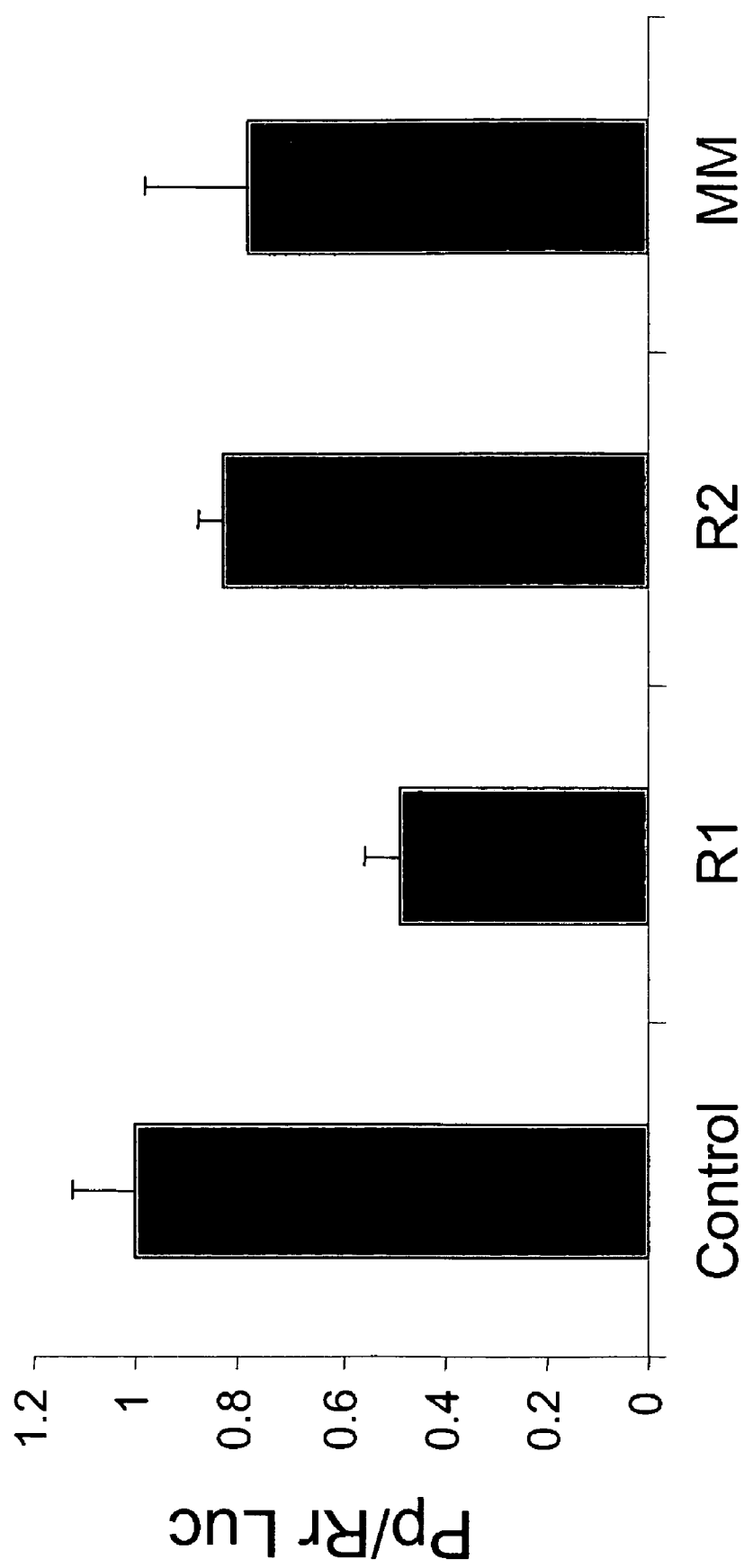
FIG. 5 depicts prolonged silencing of SOD1 by terminally-modified siRNAs.
Figure 6:
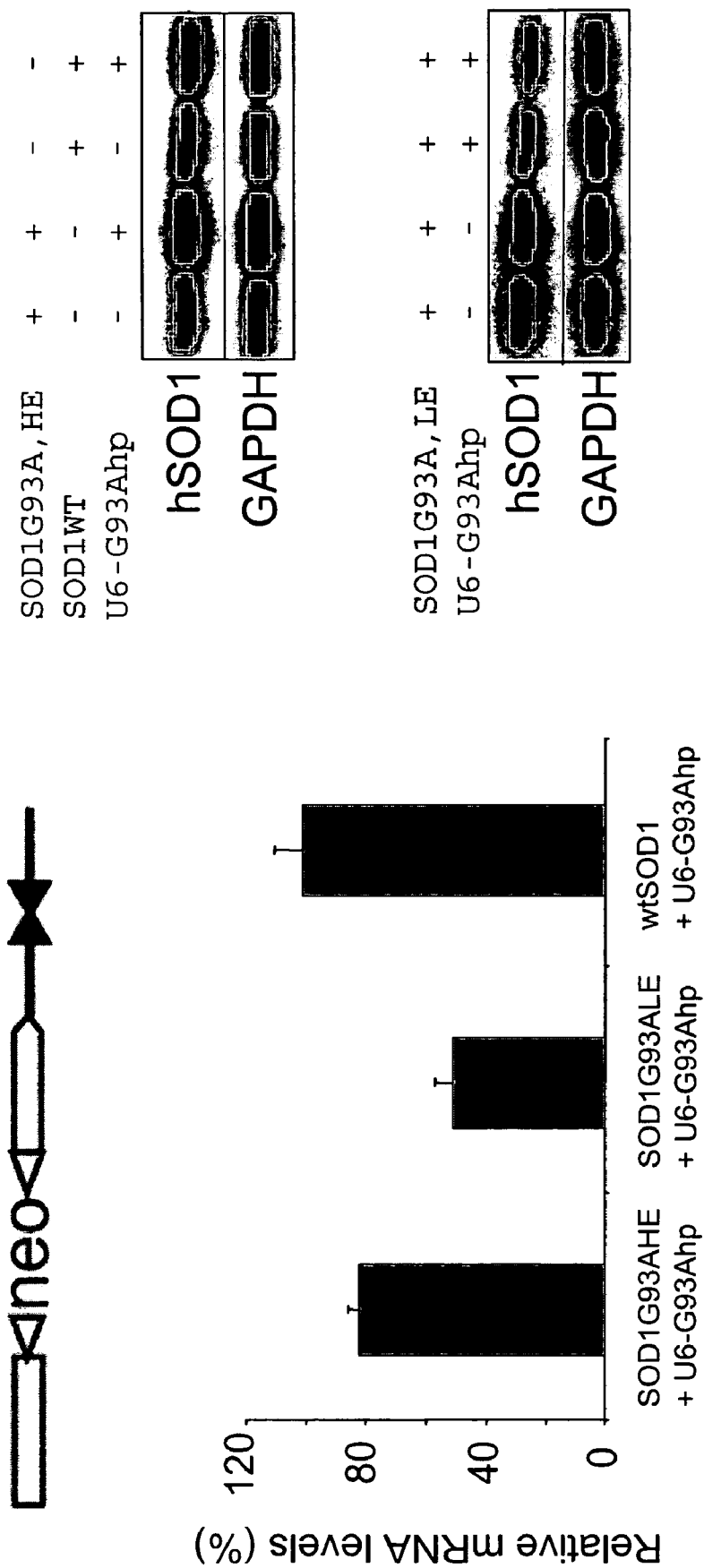
FIG. 6 illustrates that transgenic mice expressing shRNA against mutant SOD1G93A at least partially silence SOD1G93A but not wild type SOD1.
Figure 7:
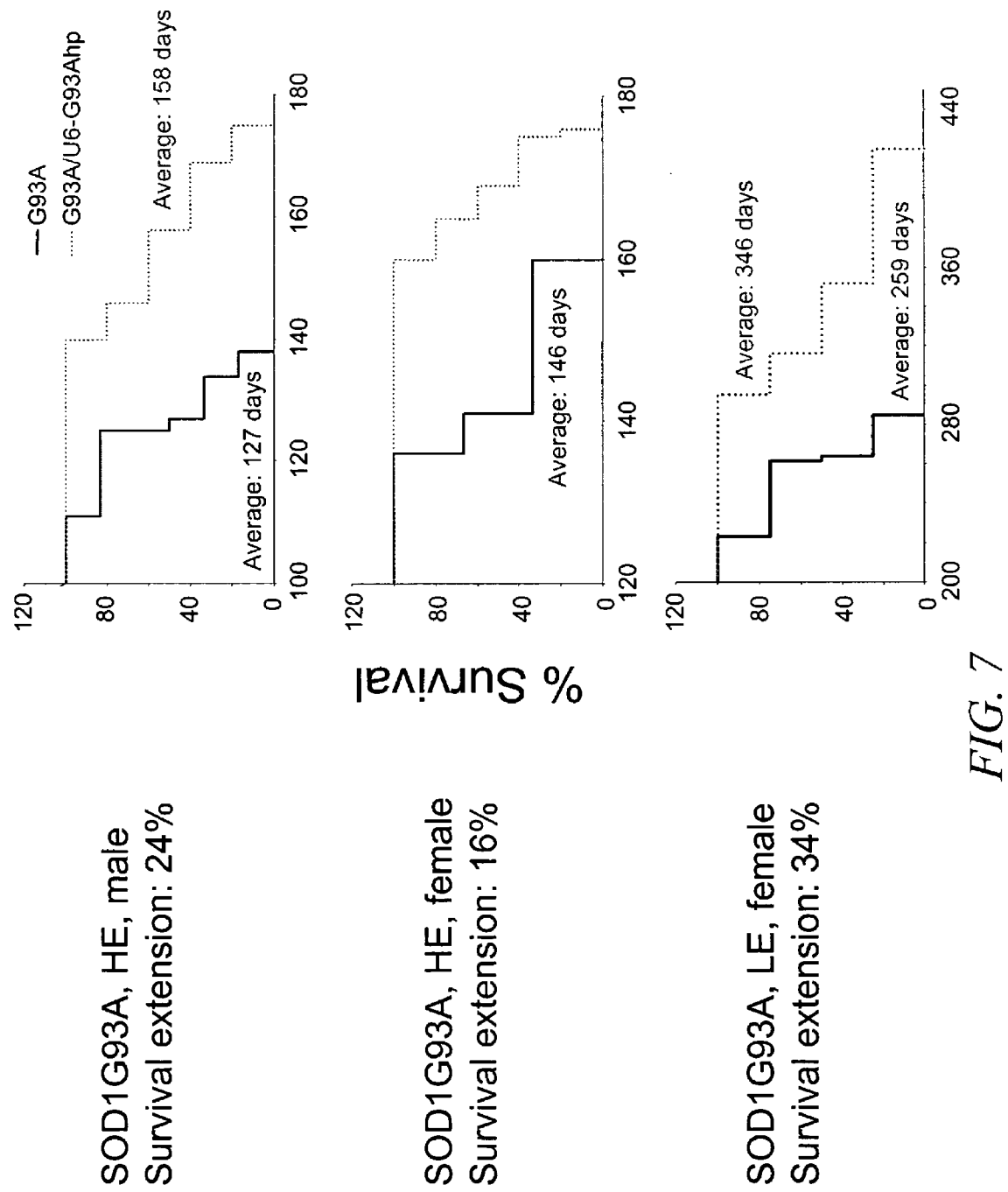
FIG. 7 is a series of graphs depicting how a decrease in the function of mutant SOD1 extends survival of mice.

In some embodiments of the present invention, the siRNA knocks down both the endogenous and the mutant mRNA. For example, as can be seen in FIGS. 3, 5 and 6, endogenous SOD can be knocked down using chemically modified siRNAs as well as unmodified shRNA. Because the half-life of the mutant is generally shorter than the half life of wild type SOD1 (i.e., the mutant is less stable than the wild type), it is believed that the RNAi agents of the present invention would selectively, or at least partially selectively knock down the function of the mutant SOD1. Knockdown of mutant SOD1 has been shown to increase life expectancy of mice by about 20-35% (see, e.g., FIG. 7) and because expression of mutant SOD1 in human is much lower than transgenic animals, it is believed, without wishing to be bound by any particular theory, that the RNAi knockdown of mutant SOD1 in humans will be more dramatic. Accordingly, a gain of 30-50% life span in ALS patients will translate into a normal human life span.

In some embodiments, siRNAs of the present invention preferentially knock down mutant SOD1 via RNAi. After introduction of siRNA into neurons, the siRNA partially unwinds, binds to the target region within both mutant and endogenous SOD1 mRNA and activates an mRNA nuclease. This nuclease cleaves the SOD1 mRNA, and cells rid themselves of partially digested mRNA, thus precluding translation, or cells digest partially translated proteins. Neurons survive on the remaining wild-type SOD1 (from the normal allele); this approach prevents the ravages of mutant SOD1 by eliminating its production.

The mRNA sequence of human SOD1 is shown in FIG. 8.

SOD-1 Mutant Gene

More than 100 SOD1 mutations have been identified. Most of these mutations produce a single amino acid replacement in the superoxide dismutase enzyme's chain of amino acids. The most common substitution, which occurs in 50 percent of American patients with type 1 amyotrophic lateral sclerosis, is the replacement of arginine with valine at position 4 in the amino acid chain (also written as Arg4Val).

SOD1 mutations affect the age when symptoms of type 1 amyotrophic lateral sclerosis begin and how fast the disease progresses. The Arg4Val mutation, for example, results in an aggressive form of the disorder with a survival time of less than 2 years after disease onset. The replacement of glycine with arginine at position 37 (Gly37Arg) is associated with early onset of the disease but a longer survival time. In addition, other factors in combination with SOD1 mutations probably vary the course of type 1 amyotrophic lateral sclerosis. For example, mutations in both the SOD1 gene and a gene known as CNTF appear to accelerate the onset of the disease.

The CNTF mutation alone has no ill effects, but in combination with the SOD1 mutation, disease symptoms appear decades earlier compared to other affected family members.

It remains unclear how SOD1 mutations lead to the selective death of motor neurons, which are the specialized nerve cells in the brain and spinal cord that control muscle movement. The superoxide dismutase enzyme is thought to gain a new (but still undefined) toxic function as a result of changes in the SOD1 gene. The malfunctioning enzyme may cause the death of motor neurons through an accumulation of harmful superoxide radicals, abnormal production of other types of toxic radicals, promotion of cell suicide (apoptosis), clumping of the enzyme with other cell proteins, or continued stimulation of motor neurons that cause them to burn out and die (excitotoxicity). Exemplary mutations to SOD1 are shown below in Table 2.

TABLE 2

SOD 1 mutations

| Location | nt | aa | | | |
|---|---|---|---|---|---|
| exon 1 | 93 | 4 | Ala4Ser | Ala4Thr | Ala4Val |
| exon 1 | 99 | 6 | Cys6Gly | Cys6Phe | |
| exon 1 | 103 | 7 | Val7Glu | | |
| exon 1 | 105 | 8 | Leu8Val | Leu8Gln | |
| exon 1 | 112 | 10 | Gly10Val | Gly10Gly | |
| exon 1 | 117 | 12 | Gly12Arg | | |
| exon 1 | 123 | 14 | Val14Met | Val14Gly | |
| exon 1 | 129 | 16 | Gly16Ser | Gly16Ala | |
| exon 1 | 142 | 20 | Phe20Cys | | |
| exon 1 | 144 | 21 | Glu21Lys | Glu21Gly | |
| exon 1 | 148 | 22 | Gln22Leu | | |
| intron 1 | 319 | | 319t>a | | |
| exon 2 | 466 | 37 | Gly37Arg | | |
| exon 2 | 469 | 38 | Leu38Val | Leu38Arg | |
| exon 2 | 478 | 41 | Gly41Ser | Gly41Asp | |
| exon 2 | 485 | 43 | His43Arg | | |
| exon 2 | 491 | 45 | Phe45Cys | | |
| exon 2 | 494 | 46 | His46Arg | | |
| exon 2 | 496 | 47 | Val47Phe | | |
| exon 2 | 500 | 48 | His48Arg | His48Gln | |
| exon 2 | 502 | 49 | Glu49Lys | | |
| exon 2 | 518 | 54 | Thr54Arg | | |
| exon 3 | 645 | 59 | Ser59Ile | Ser59Ser | |
| exon 3 | 663 | 65 | Asn65Ser | | |
| exon 3 | 669 | 67 | Leu67Arg | | |
| exon 3 | 683 | 72 | Gly72Cys | Gly72Ser | |
| exon 3 | 695 | 76 | Asp76Tyr | Asp76Val | |
| exon 4 | 1048 | 80 | His80Arg | | |
| exon 4 | 1059 | 84 | Leu84Val | Leu84Phe | |
| exon 4 | 1062 | 85 | Gly85Arg | | |
| exon 4 | 1066 | 86 | Asn86Ser | | |
| exon 4 | 1068 | 87 | Val87Met | Val87Ala | |
| exon 4 | 1071 | 88 | Thr88delACTGCTGAC | | |
| exon 4 | 1074 | 89 | Ala89Thr | Ala89Val | |
| exon 4 | 1078 | 90 | Asp90Ala | Asp90Val | |
| exon 4 | 1086 | 93 | Gly93Cys | Gly93Arg | Gly93Ser |
| | | | Gly93Asp | Gly93Ala | Gly93Val |
| exon 4 | 1092 | 95 | Ala95Thr | | |
| exon 4 | 1095 | 96 | Asp96Asn | | |
| exon 4 | 1098 | 97 | Val97Met | | |
| exon 4 | 1107 | 100 | Glu100Lys | Glu100Gly | |
| exon 4 | 1110 | 101 | Asp101Asn | Asp101Gly | |
| exon 4 | 1119 | 104 | Ile104Phe | | |
| exon 4 | 1122 | 105 | Ser105delTCACTC | Ser105Leu | |
| exon 4 | 1125 | 106 | Leu106Val | | |
| exon 4 | 1132 | 108 | Gly108Val | | |
| exon 4 | 1144 | 112 | Ile112Thr | Ile112Met | |
| exon 4 | 1146 | 113 | Ile113Phe | Ile113Thr | |
| exon 4 | 1150 | 114 | Gly114Ala | | |
| exon 4 | 1152 | 115 | Arg115Gly | | |
| exon 4 | 1161 | 118 | Val118Leu | Val118insAAAC | |
| intron 4 | 1415 | | 1415t>g | | |
| exon 5 | 1441 | 124 | Asp124Gly | Asp124Val | |
| exon 5 | 1443 | 125 | Asp125His | | |
| exon 5 | 1446 | 126 | Leu26delTT | Leu26STOP | Leu26Ser |
| exon 5 | 1450 | 127 | Gly127insTGGG | | |
| exon 5 | 1465 | 132 | Glu132insTT | | |
| exon 5 | 1467 | 133 | Glu133del | | |
| exon 5 | 1471 | 134 | Ser134Asn | | |
| exon 5 | 1487 | 139 | Asn139Asn | Asn139Lys | |
| exon 5 | 1489 | 140 | Ala140Gly | Ala140Ala | |
| exon 5 | 1491 | 141 | Gly141STOP | | |
| exon 5 | 1501 | 144 | Leu144Ser | Leu144Phe | |
| exon 5 | 1503 | 145 | Ala145Thr | Ala145Gly | |
| exon 5 | 1506 | 146 | Cys146Arg | | |
| exon 5 | 1509 | 147 | Gly147Arg | | |
| exon 5 | 1512 | 148 | Val148Ile | Val148Gly | |
| exon 5 | 1516 | 149 | Ile149Thr | | |
| exon 5 | 1522 | 151 | Ile151Thr | Ile151Ser | |
| exon 5 | 1529 | 153 | Gln153Gln | | |

Methods of Treatment:

The present invention provides for both prophylactic and therapeutic methods of treating a subject at risk of (or susceptible to) a disorder or having a disorder associated with aberrant or unwanted target gene expression or activity. "Treatment", or "treating" as used herein, is defined as the application or administration of a therapeutic agent (e.g., nucleic acid molecule, and/or a pharmaceutical agent) to a patient, or application or administration of a therapeutic agent to an isolated tissue or cell line from a patient, who has a disease or disorder, a symptom of disease or disorder or a predisposition toward a disease or disorder, with the purpose to cure, heal, alleviate, delay, relieve, alter, remedy, ameliorate, improve or affect the disease or disorder, the symptoms of the disease or disorder, or the predisposition toward disease.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with the nucleic acid molecules and/or pharmaceutical agents of the present invention or target nucleic acid molecules and/or pharmaceutical agents according to that individual's drug response genotype. Pharmacogenomics allows a clinician or physician to target prophylactic or therapeutic treatments to patients who will most benefit from the treatment and to avoid treatment of patients who will experience toxic drug-related side effects.

a) Prophylactic Methods

In one aspect, the invention provides a method for preventing in a subject, a disease or condition associated with an aberrant or unwanted target gene expression or activity, by administering to the subject a therapeutic agent (e.g., a nucleic acid molecule, and/or a pharmaceutical agent). Subjects at risk for a disease which is caused or contributed to by aberrant or unwanted target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject. The appropriate agent can be determined based on screening assays described herein.

b) Therapeutic Methods

Another aspect of the invention pertains to methods of modulating target gene expression, protein expression or activity for therapeutic purposes. Accordingly, in an exemplary embodiment, the modulatory method of the invention involves contacting a cell capable of expressing the target gene with a therapeutic agent (e.g., a nucleic acid molecule and/or pharmaceutical agent) that is specific for the target gene or protein (e.g., is specific for the mRNA encoded by said gene or specifying the amino acid sequence of said protein) such that expression or one or more of the activities of target protein is modulated. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

c) Pharmacogenomics

The therapeutic agents (e.g., nucleic acid molecules and/or pharmaceutical agents) of the invention can be administered to individuals to treat (prophylactically or therapeutically) disorders associated with aberrant or unwanted target gene activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10-11): 983-985 and Linder, M. W. et al. (1997) Clin. Chem. 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a target gene polypeptide of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a therapeutic agent of the present invention can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a therapeutic agent, as described herein.

Therapeutic agents can be tested in an appropriate animal model. For example, an siRNA (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

Disease Indications

The compositions of the invention can act as novel therapeutic agents for controlling one or more of cellular proliferative and/or differentiative disorders, disorders associated with bone metabolism, immune disorders, hematopoietic disorders, cardiovascular disorders, liver disorders, viral diseases, pain or metabolic disorders.

In some embodiments, the present invention acts as a therapeutic agent agains ALS. Amyotrophic lateral sclerosis (ALS) is a chronic, progressive disease marked by gradual degeneration of nerve cells in the central nervous system that control voluntary muscle movement. In ALS patients, degeneration and loss of motorneurons occurs primarily in the anterior horn of the spinal cord and of the brainstem and, to a variable extent, in the descending motor pathways within the cortico-spinal tract (Deng et al., 1993; Rothstein et al., 1995).

ALS leads to progressive muscular atrophy, weakness, paralysis and eventually death due to respiratory failure.

ALS occurs in two forms: familial ALS (FALS), and sporadic ALS (SALS). FALS comprises 5-10% of all cases, with an autosomal dominant pattern of inheritance (Gurney et al., 1994; Rosen et al., 1993). Approximately 20% of all FALS cases are associated with mutations in the SOD1 gene.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer," "hyperproliferative," and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

In general, the compositions of the invention are designed to target genes associated with particular disorders. Examples of such genes associated with proliferative disorders that can be targeted include activated ras, p53, BRCA-1, and BRCA-2. Other specific genes that can be targeted are those associated with amyotrophic lateral sclerosis (ALS; e.g., superoxide dismutase-1 (SOD1)); Huntington's disease (e.g., huntingtin), Parkinson's disease (parkin), and genes associated with autosomal dominant disorders.

The compositions of the invention can be used to treat a variety of immune disorders, in particular those associated with overexpression of a gene or expression of a mutant gene. Examples of hematopoietic disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, congestive heart failure, coronary artery disease, valvular disease, arrhythmias, and cardiomyopathies.

Disorders which may be treated by methods described herein include, but are not limited to, disorders associated with an accumulation in the liver of fibrous tissue, such as that resulting from an imbalance between production and degradation of the extracellular matrix accompanied by the collapse and condensation of preexisting fibers.

Additionally, molecules of the invention can be used to treat viral diseases, including but not limited to hepatitis B, hepatitis C, herpes simplex virus (HSV), HIV-AIDS, poliovirus, and smallpox virus. Molecules of the invention are engineered as described herein to target expressed sequences of a virus, thus ameliorating viral activity and replication. The molecules can be used in the treatment and/or diagnosis of viral infected tissue. Also, such molecules can be used in the treatment of virus-associated carcinoma, such as hepatocellular cancer.

Nanotransporters

In one embodiment, the present invention relates to nanotransporters. The nanotransporters of the present invention comprise a central core with at least one functional surface group attached. Various molecules can be associated with the nanotransporter for delivery to a desired target, e.g., a cell or tissue. Molecules capable of associating with the nanotransporter include, but are not limited to, nucleic acid molecules and/or pharmaceutical agents.

In one embodiment, the core of the nanotransporter is a nanotube, e.g., a carbon nanotube. Nanotubes for use in the present invention may be either single walled ("SWNTs") or multi-walled ("MWNTs"). A SWNT is a single tube that is about 1 nanometer in diameter and about 1 to about 100 microns in length. MWNTs are tubes with at least one other tube embedded within it.

In one embodiment, the core of the nanotransporter is a nanoparticle. Nanoparticles of the present invention include, but are not limited to, dendrimers. Dendrimers are highly branched polymers with a well-defined architecture. Many dendrimers are commercially available. The dendrimers of the invention include but are not limited to: polylysine dendrimers, Polyamidoamine (PAMAM): Amine terminated and/or PAMAM: Carboxylic acid terminated (available, e.g., from Dendritech, Inc., Midland, Mich.); Diaminobutane (DAB)-DAB: Amine terminated and/or DAB: Carboxylic acid terminated; and PEGs: OH terminated (Frechet et al., JACS 123:5908 (2001)), among others. In one embodiment, polylysine dendrimers or a variant thereof are used.

In one aspect of the invention, various functional surface groups are conjugated to the core of the nanotransporter. As used herein, the term "functional surface group" refers to molecules that upon binding to the core increase the functionality of the nanotransporter, e.g., to increase cell targeting specificity, to increase delivery of the nanotransporter to the target cell, and/or to impart a precise biological function. Examples of functional surface groups of the invention include, but are not limited to, lipids, fatty acids and derivatives, fluorescent and charge controlling molecules, and cell type specific targeting moieties. In the present invention, a single type of functional surface group or multiple types of functional surface groups may be present on the surface of the core of the nanotransporter.

Exemplary nanotransporters and corresponding delivery complexes may be found, for example, in U.S. Ser. No. 11/699,177, filed Jan. 26, 2007, the content of which is hereby incorporated by this reference in its entirety.

Methods of Introducing RNAi Agents

Physical methods of introducing the RNAi agents of the present invention include injection of a solution containing the RNA, bombardment by particles covered by the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical- mediated transport, such as calcium phosphate, and the like. Thus the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly); or introduced extracellularly into a cavity, interstitial space, into the circulation of an organism. Vascular or extravascular circulation, the blood or lymph system, and the cerebrospinal fluid are sites where the RNA may be introduced.

The cell with the target gene may be derived from or contained in any organism, including animals. Preferred are vertebrate animals. Examples of vertebrate animals include, but are not limited to, fish, mammal, cattle, goat, pig, sheep, rodent, hamster, mouse, rat, primate, and human. The agents of the instant invention are especially suited for use in humans.

Depending on the particular target gene and the dose of double stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

Quantitation of the amount of gene expression allows one to determine a degree of inhibition which is greater than 10%, 33%, 50%, 90%, 95% or 99% as compared to a cell or organism not treated according to the present invention. Lower doses of injected material and longer times after administration of siRNA may result in inhibition in a smaller percentage of inhibition (e.g., at least 10%, 20%, 50%, 75%, 90%, or 95% inhibition). Quantitation of gene expression may show similar amounts of inhibition at the level of accumulation of target mRNA or translation of target protein. As an example, the efficiency of inhibition may be determined by assessing the amount of gene product, for example in a cell or sample derived from a treated organism; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

Pharmaceutical Compositions

The invention pertains to uses of the above-described agents for therapeutic treatments as described infra. Accordingly, the agents of the present invention can be incorporated into pharmaceutical compositions suitable for administration. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, intraperitoneal, intramuscular, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The compounds can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

In some embodiments, the siRNAs (and other optional pharmacological agents) can be delivered directly via a pump device. For example, in some embodiments, the chemically modified siRNAs of the invention are delivered directly by infusion into the spinal cord, e.g., for neurodegenerative disease such as ALS, Huntingtons Disease, Alzheimer's Disease or the like. In some embodiments, the siRNAs delivered via a pump device are associated in some manner with a nanotransporter.

The compounds can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the compound which achieves a half-maximal inhibition of symptoms) as determined in cell culture. Such information can be used to more accurately determine useful doses in humans. Levels in plasma may be measured, for example, by high performance liquid chromatography.

A therapeutically effective amount of a composition containing a compound of the invention (e.g., a siRNA, candidate siRNA derivative, modified siRNA, etc.) (i.e., an effective dosage) is an amount that inhibits expression of the polypeptide encoded by the target gene by at least 30 percent. Higher percentages of inhibition, e.g., 45, 50, 75, 85, 90 percent or higher may be preferred in certain embodiments. Exemplary doses include milligram or microgram amounts of the molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. The compositions can be administered one time per week for between about 1 to 10 weeks, e.g., between 2 to 8 weeks, or between about 3 to 7 weeks, or for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments.

It is furthermore understood that appropriate doses of a composition depend upon the potency of composition with respect to the expression or activity to be modulated. When one or more of these molecules is to be administered to an animal (e.g., a human) to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration.

Screening Assays

The methods of the invention are also suitable for use in methods to identify and/or characterize potential pharmacological agents, e.g. identifying new pharmacological agents from a collection of test substances and/or characterizing mechanisms of action and/or side effects of known pharmacological agents.

Thus, the present invention also relates to a system for identifying and/or characterizing pharmacological agents acting on at least one target protein comprising: (a) a eukaryotic cell or a eukaryotic non-human organism capable of expressing at least one endogenous target gene coding for said so target protein, (b) at least one siRNA molecule capable of inhibiting the expression of said at least one endogenous target gene, and (c) a test substance or a collection of test substances wherein pharmacological properties of said test substance or said collection are to be identified and/or characterized. Further, the system as described above preferably comprises: (d) at least one exogenous target nucleic acid coding for the target protein or a variant or mutated form of the target protein wherein said exogenous target nucleic acid differs from the endogenous target gene on the nucleic acid level such that the expression of the exogenous target nucleic acid is substantially less inhibited by the siRNA molecule than the expression of the endogenous target gene.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) Nature 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.)).

In a preferred embodiment, the library is a natural product library, e.g., a library produced by a bacterial, fungal, or yeast culture. In another preferred embodiment, the library is a synthetic compound library.

This invention is further illustrated by the following examples which should not be construed as limiting.

EXEMPLIFICATION

Materials and Methods siRNA Preparation 21-nucleotide RNAs were chemically synthesized as 2' bis(acetoxyethoxy)-methyl ether-protected oligos by Dharmacon (Lafayette, Colo.). Synthetic oligonucleotides were deprotected, annealed and purified as described by the manufacturer. Successful duplex formation was confirmed by 20% non-denaturing polyacrylamide gel electrophoresis (PAGE). All siRNAs were stored in DEPC (0.1% diethyl pyrocarbonate)-treated water at −80° C. The sequences of GFP or RFP target-specific siRNA duplexes were designed according to the manufacturer's recommendation and subjected to a BLAST search against the human genome sequence to ensure that no endogenous genes of the genome were targeted.

Culture and Transfection of Cells

Hela cells were maintained at 37° C. in Dulbecco's modified Eagle's medium (DMEM, Invitrogen) supplemented with 10% fetal bovine serum (FBS), 100 units/ml penicillin and 100 μg/ml streptomycin (Invitrogen). Cells were regularly passaged at sub-confluence and plated 16 hr before transfection at 70% confluency. Lipofectamine (Invitrogen)-mediated transient cotransfections of reporter plasmids and siRNAs were performed in duplicate 6-well plates as described by the manufacturer for adherent cell lines. A transfection mixture containing 0.16-0.66 μg pEGFP-C1 and 0.33-1.33 μg pDsRed1-N1 reporter plasmids (Clontech), various amounts of siRNA (1.0 nM-200 nM), and 10 μl lipofectamine in 1 ml serum-reduced OPTI-MEM (Invitrogen) was added to each well. Cells were incubated in transfection mixture for 6 hours and further cultured in antibiotic-free DMEM. Cells were treated under same conditions without siRNA for mock experiments. At various time intervals, the transfected cells were washed twice with phosphate buffered saline (PBS, Invitrogen), flash frozen in liquid nitrogen, and stored at −80° C. for reporter gene assays.

Example 1

Terminally-Modified siRNAs (tmsiRNA) Effectively Silenced Target mRNA In Vitro and In Vivo Two terminally-modified siRNAs, R1 and R2, directed to different portions of the SOD 1 target were generated to evaluate their RNA silencing properties. Both R1 (see FIG. 1A) and R2 (see FIG. 1B) contained 3-5 modified nucleotides at the 5' and 3' ends of both strands of the siRNA duplex. R1 and R2 contain internal nucleotides which are perfectly complementary to SOD1, while Mm contains mismatches among the internal nucleotides. Fluorescent labels were conjugated to the 5' terminus of each terminally-modified siRNA. Firefly luciferase (Pp) with SOD1 target sequence placed in the 3' UTR and *Renilla* luciferase (Rr) constructs were co-transfected into HEK293 cells with various siRNAs (modified R1 and R2 or mismatch). Control was cells transfected with luciferase constructs but no modified siRNA. The luciferase activity was measured 24 h post-transfection. The efficiencies were evaluated at two concentrations (20 nM and 100 nM) (see FIG. 2). These results indicate that both terminally-modified siRNAs against SOD1 inhibit reporter gene expression with efficiency similar to the unmodified siRNAs in cells. To determine whether these msiRNAs could knockdown endogenous SOD1, R1 and R2 were transfected into HEK293 cells, harvested, and endogenous J SOD1 protein levels were measured by Western blot (see FIG. 3). R1 and R2 were also administered into transgenic mice expressing mutant SOD1G93A by intrathecal infusion using a miniosmotic pump. R1 was infused at 0.7 mg/day/animal; R2 and Mm were infused at 0.4 mg/day/animal; control "C" was PBS. Eight days after the infusion, the spinal cord was dissected and mutant SOD1 levels were measured (see FIG. 3B). These results indicate that while R2 shows only marginal knockdown of endogenous SOD1, R1 shows marked knockdown of endogenous SOD1. Further, terminally-modified siRNA R1 knocked down mutant SOD1 levels by 30% in vivo. Together, these results indicate that terminally-modified R1 can mediate long term RNAi against mutant SOD1 in vitro and in vivo.

Example II

Terminally-Modified siRNAs have a Low Toxicity Profile

Figure 4:
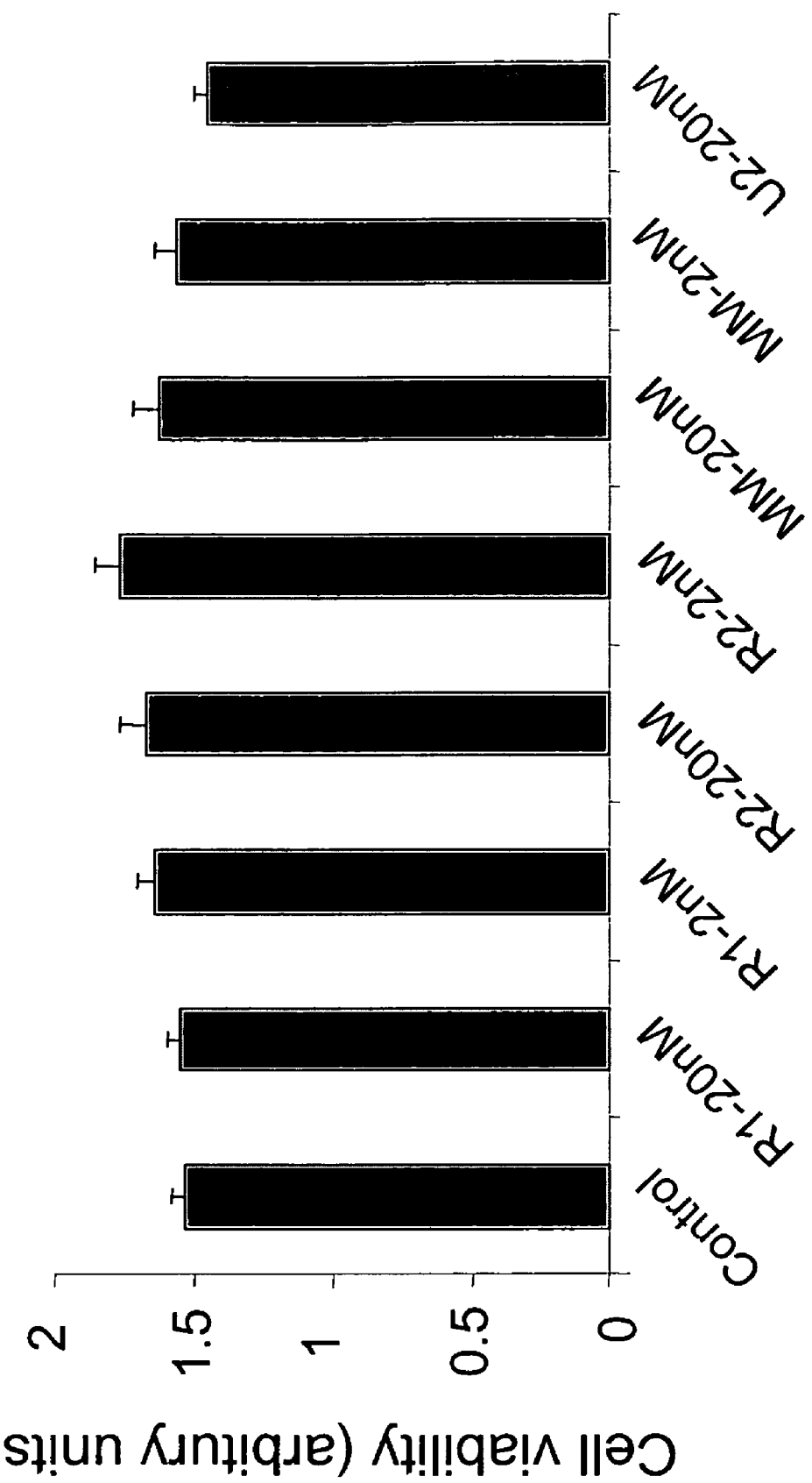
FIG. 4 depicts cell viability results after transfection with terminally-modified siRNAs compared to their corresponding unmodified siRNAs, mismatch siRNA, and control.

HEK293 cells were transfected with terminally-modified siRNAs, R1 and R2, their corresponding unmodified siRNAs, mismatch siRNA, or control (transfection agent alone). Cells were transfected with two different concentrations (2 nM and 20 nM). Cell viability was measured 24 h post-transfection (see FIG. 4). These results indicate that terminally-modified siRNAs are not toxic to cells.

Example III

Terminally-Modified siRNAs Exhibit Prolonged Silencing Activity In Vitro

To determine the duration of the silencing of SOD1 by R1 and R2 compared to the mismatch siRNA, HEK293 cells were transfected and silencing activity was measured by the dual luciferase assay (see FIG. 5). Terminally-modified siRNAs (20 nM) were transfected into HEK293 cells 7 days before Pp and Rr constructs were transfected. Luciferase activity was measured 24 h after Pp and Rr transfection. These results indicate that R1 effectively silences SOD1 seven days after transfection.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The contents of all references, patents, and patent applications cited throughout this application are hereby incorporated by reference.

What is claimed:

1. A method of treating ALS in a subject, comprising administering to said subject a small interfering RNA (siRNA) comprising a sense strand and an antisense strand, wherein
   (a) the antisense strand has a sequence sufficiently complementary to a SOD1 target mRNA sequence to direct target-specific RNA interference (RNAi) of mutant and wild-type SOD1 mRNA;
   (b) the strands are modified at both ends with more than one chemically modified nucleotide such that in vivo stability is enhanced as compared to a corresponding unmodified siRNA; and
   (c) the antisense strand retains the ability to form an A-form helix when in association with the target mRNA; and,
   (d) both the sense strand and the antisense strand are strands according to formula IV:

$$5'\text{-}(c)_m\text{-}[5'\text{ Seq}]\text{-}[\text{Core Seq}]\text{-}[3'\text{ Seq}]\text{-}(c)_m\text{-}3' \quad (IV)$$

wherein:
   (i) each occurrence of c is independently an end modification;
   (ii) each occurrence of m is 1;
   (iii) -5'Seq- is represented by the formula:

$$5'\text{-}N_1\text{-}(L_2\text{-}N_2)_n\text{-}(L_3\text{-}N_3)_p\text{-}3'$$

wherein:
   n is an integer from 2-6;
   p is an integer from 0-3;
   $N_1$ is an unmodified nucleotide;
   each occurrence of $N_2$ is independently selected from the group consisting of a modified purine nucleotide, an unmodified purine nucleotide and a modified pyrimidine nucleotide, wherein about 1-6 occurrences of $N_2$ are modified pyrimidine nucleotides;
   each occurrence of $N_3$ is independently selected from the group consisting of a modified purine nucleotide, an unmodified purine nucleotide, a modified pyrimidine nucleotide and an unmodified pyrimidine nucleotide; and
   each occurrence of $L_2$ and $L_3$ are independently a phosphate linkage, or a linkage according to formula III;

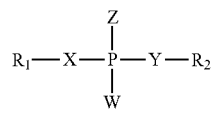
                                            III (iv) -CoreSeq- is represented by the formula:

5'-(L₄-N₄)$_q$-3' wherein:
  q is an integer from 5-15;
  each occurrence of N₄ is an unmodified nucleotide; and
  each occurrence of L₄ is independently a phosphate linkage; and (v) -3' Seq- is represented by the formula:

5'-(L₅-N₅)$_r$-(L₆-N₆)$_s$-L₇-N₇-3' wherein:
  r is an integer from 3-6;
  s is an integer from 0 to 3;
  N₇ is an unmodified nucleotide;

each occurrence of N₅ is independently selected from the group consisting of a modified purine nucleotide, an unmodified purine nucleotide and a modified pyrimidine nucleotide, wherein about 1-6 occurrences of N₅ are modified pyrimidine nucleotides;

each occurrence of N₆ is independently selected from the group consisting of a modified purine nucleotide, an unmodified purine nucleotide, a modified pyrimidine nucleotide and an unmodified pyrimidine nucleotide;

each occurrence of L₅, L₆ and L₇ are independently a phosphate linkage or a linkage according to formula III, said siRNA being administered in an amount sufficient for degradation of the target mRNA to occur, thereby treating ALS in the subject, wherein the siRNA is R1, wherein the sense strand comprises the sequence set forth as SEQ ID NO:5, and the antisense strand comprises the sequence set forth as SEQ ID NO:6.

\* \* \* \* \*

UNITED STATES PATENT AND TRADEMARK OFFICE
CERTIFICATE OF CORRECTION

| | | |
|---|---|---|
| PATENT NO. | : 7,951,784 B2 | Page 1 of 1 |
| APPLICATION NO. | : 11/698785 | |
| DATED | : May 31, 2011 | |
| INVENTOR(S) | : Tariq M. Rana et al. | |

It is certified that error appears in the above-identified patent and that said Letters Patent is hereby corrected as shown below:

At column 59, lines 3 to 6, the left-hand formula should appear as follows:

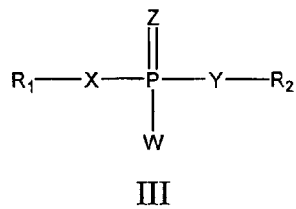

III

Signed and Sealed this
Sixteenth Day of August, 2011

David J. Kappos
*Director of the United States Patent and Trademark Office*